US012606612B2

(12) United States Patent
Weiner et al.

(10) Patent No.: US 12,606,612 B2
(45) Date of Patent: Apr. 21, 2026

(54) MULTIVALENT DNA ANTIBODY CONSTRUCTS AND USE THEREOF

(71) Applicant: THE WISTAR INSTITUTE OF ANATOMY AND BIOLOGY, Philadelphia, PA (US)

(72) Inventors: David Weiner, Merion, PA (US); Elizabeth Parzych, Philadelpha, PA (US); Ami Patel, Philadelphia, PA (US)

(73) Assignee: The Wistar Institute of Anatomy and Biology, Philadelphia, PA (US)

( * ) Notice: Subject to any disclaimer, the term of this patent is extended or adjusted under 35 U.S.C. 154(b) by 867 days.

(21) Appl. No.: 17/631,709

(22) PCT Filed: Jul. 31, 2020

(86) PCT No.: PCT/US2020/044396

§ 371 (c)(1),
(2) Date: Jan. 31, 2022

(87) PCT Pub. No.: WO2021/022107

PCT Pub. Date: Feb. 4, 2021

(65) Prior Publication Data

US 2022/0324948 A1 Oct. 13, 2022

Related U.S. Application Data

(60) Provisional application No. 62/881,173, filed on Jul. 31, 2019.

(51) Int. Cl.
*C07K 16/12* (2006.01)
*A61P 31/00* (2006.01)
*C07K 16/1217* (2026.01)

(52) U.S. Cl.
CPC .......... *C07K 16/1217* (2013.01); *A61P 31/00* (2018.01); *C07K 2317/524* (2013.01); *C07K 2317/526* (2013.01); *C07K 2317/72* (2013.01)

(58) Field of Classification Search
None
See application file for complete search history.

(56) References Cited

U.S. PATENT DOCUMENTS

| | | | |
|---|---|---|---|
| 2005/0112139 A1* | 5/2005 | Karp | A61P 37/00 |
| | | | 424/188.1 |
| 2015/0284448 A1 | 10/2015 | Weiner | |
| 2016/0355586 A1 | 12/2016 | Johnson | |
| 2017/0275639 A1 | 9/2017 | Chen | |
| 2018/0118836 A1 | 5/2018 | Bernett | |

FOREIGN PATENT DOCUMENTS

| | | | | |
|---|---|---|---|---|
| WO | 2017193101 A1 | 11/2017 | | |
| WO | WO-2017192946 A1 * | 11/2017 | ............. | A61P 31/16 |
| WO | 2019067805 | 4/2019 | | |
| WO | 2019099852 | 5/2019 | | |
| WO | WO-2019099852 A1 * | 5/2019 | ............. | A61P 31/04 |

OTHER PUBLICATIONS

Freudl et al. Microb Cell Fact (2018) 17:52, 10 pages.*
Edwards et al. J. Mol. Biol. (2003) 334, 103-118.*
Chakraborti Srinjoy: "Therapeutic Antibody Against Neisseria gonorrhoeae Lipooligosaccharide, a Phase-variable Virulence Factor", GSBS Dissertations and Theses, Jan. 1, 2017 (Jan. 1, 2017), 215 pages.
Gulati et al., "Immunization against a saccharide epitope accelerates clearance of experimental gonococcal infection," PLoS Pathog. 2013;9(8):e1003559. Epub Aug. 29, 2013 (pp. 1-11).
Gulati S et al., "Complement alone drives efficacy of a chimeric antigonococcal monoclonal antibody", PLoS Biology, vol. 17, No. 6, 19 (Jun. 19, 2019), 29 pages, p. e3000323.

* cited by examiner

*Primary Examiner* — Oluwatosin A Ogunbiyi
(74) *Attorney, Agent, or Firm* — Riverside Law LLP

(57) ABSTRACT

Disclosed herein are compositions for generating a synthetic antibody or synthetic multivalent antibody in a subject. Also disclosed are methods for generating a synthetic antibody or synthetic multivalent antibody in a subject by administering a composition including one or more recombinant nucleic acid sequence that encodes a synthetic antibody or synthetic multivalent antibody to the subject. The disclosure also provides a compositions and methods of preventing and/or treating a *Neisseria gonorrhoeae* infection in a subject using said synthetic antibody or synthetic multivalent antibody.

19 Claims, 11 Drawing Sheets

Specification includes a Sequence Listing.

| Tube | | Day | Mouse | DMAb | | Cage | Early | Peak | Late |
|---|---|---|---|---|---|---|---|---|---|
| 1 | A-F | 0 | Jh | | | 66/67 | | | |
| 2 | A-C | 3 | Jh | 2C7 | wt | 58 | | | |
| 3 | A-C | 3 | Jh | 2C7 | E430G | 66 | | | |
| 4 | A-C | 3 | Jh | 2C7 | E345K | 67 | | | |
| 5 | A-C | 3 | Jh | 2C7 | RGY | 59 | | | |
| 6 | A-C | 21 | Jh | 2C7 | wt | 58 | | | |
| 7 | A-C | 21 | Jh | 2C7 | E430G | 66 | | | |
| 8 | A-C | 21 | Jh | 2C7 | E345K | 67 | | | |
| 9 | A-C | 21 | Jh | 2C7 | RGY | 59 | | | |
| 10 | A-C | 92 | Jh | 2C7 | wt | 58 | | | |
| 11 | A-C | 35 | Jh | 2C7 | E430G | 66 | | | |
| 12 | A-C | 35 | Jh | 2C7 | E345K | 67 | | | |
| 13 | A-C | 92 | Jh | 2C7 | RGY | 59 | | | |

Fig. 4

MULTIVALENT DNA ANTIBODY CONSTRUCTS AND USE THEREOF

CROSS-REFERENCE TO RELATED APPLICATIONS

This application is the U.S. national phase application filed under 35 U.S.C. § 371 claiming benefit to International Patent Application No. PCT/US2020/044396, filed on Jul. 31, 2020, which is entitled to priority to U.S. Application No. 62/881,173, filed Jul. 31, 2019, the disclosures of which are incorporated herein by reference in their entirety.

REFERENCE TO A "SEQUENCE LISTING," A TABLE, OR A COMPUTER PROGRAM LISTING APPENDIX SUBMITTED AS AN ASCII TEXT FILE

The Sequence Listing written in the ASCII text file: 206194-0038-00US_SequenceListing.txt created on Jan. 24, 2022, and 34,254 bytes in size, is hereby incorporated by reference.

TECHNICAL FIELD

The present invention relates to compositions comprising recombinant nucleic acid sequences for generating one or more synthetic multivalent antibodies, or functional fragments thereof, in vivo, and methods of use thereof for preventing and/or treating a disease or disorder in a subject by administering said composition.

BACKGROUND

*Neisseria gonorrhoeae*, which causes over 75 million new gonorrhea infections each year, is considered an urgent health threat due to rising levels of multi-drug resistant strains. With only a single effective treatment regimen remaining, new strategies to combat this pathogen are desperately needed.

Thus there is need in the art for improved therapeutics that prevent and/or treat *Neisseria gonorrhoeae* infection. The current invention satisfies this need.

SUMMARY

In one embodiment, the invention relates to a nucleic acid molecule encoding one or more synthetic antibodies or fragment thereof, wherein the nucleic acid molecule comprises a nucleotide sequence encoding a synthetic antibody or a nucleotide sequence encoding a fragment of a synthetic antibody. In one embodiment, the one or more synthetic antibodies is a monoclonal antibody, monofunctional antibody, bifunctional antibody, bispecific antibody, multivalent antibody, defucosylated antibody, non-fucosylated antibody, an immunoglobulin, or any combination thereof.

In one embodiment, the nucleic acid molecule encodes a fragment of a multivalent antibody. In one embodiment, the multivalent antibody is a hexameric antibody that forms in vivo. In one embodiment, the nucleic acid molecule encodes a heavy chain of a multivalent antibody comprising a variation of at least one Fc residue of Q311, A339, E430, E345, D356, I253, S254, Y436, Q386, E382, or S440. In one embodiment, the nucleic acid molecule encodes a heavy chain of a multivalent antibody comprising a variation of at least one Fc residue of E345K, E430G, or S440Y.

In one embodiment, the nucleic acid molecule encodes one or more synthetic antibodies, or fragments thereof, wherein the nucleic acid molecule comprises a nucleotide sequence encoding an anti-*Neisseria gonorrhoeae* synthetic antibody. In one embodiment, the nucleic acid molecule encodes one or more synthetic antibodies, or fragments thereof, wherein the nucleic acid molecule comprises a nucleotide sequence encoding a fragment of an anti-*Neisseria gonorrhoeae* synthetic antibody. In one embodiment, the nucleic acid molecule encodes one or more synthetic antibodies, or fragments thereof, wherein the nucleic acid molecule comprises a variant of nucleotide sequence encoding an anti-*Neisseria gonorrhoeae* synthetic antibody. In one embodiment, the nucleic acid molecule encodes one or more synthetic antibodies, or fragments thereof, wherein the nucleic acid molecule comprises a variant of a nucleotide sequence encoding a fragment of an anti-*Neisseria gonorrhoeae* synthetic antibody.

In one embodiment, the nucleic acid molecule comprises a nucleotide sequence encoding a light chain of an anti-*Neisseria gonorrhoeae* antibody. In one embodiment, the nucleic acid molecule comprises a nucleotide sequence encoding a heavy chain of an anti-*Neisseria gonorrhoeae* antibody.

In one embodiment, the nucleic acid molecule comprises a nucleotide sequence encoding an amino acid sequence having at least about 95% identity over an entire length of the amino acid sequence SEQ ID NO:2.

In one embodiment, the nucleic acid molecule comprises a nucleotide sequence encoding an amino acid sequence having at least about 95% identity over an entire length of the amino acid sequence of SEQ ID NO:4, SEQ ID NO:6, SEQ ID NO:8, SEQ ID NO:10 or SEQ ID NO:12.

In one embodiment, the nucleic acid molecule comprises a nucleotide sequence having at least about 95% identity over an entire length of the nucleic acid sequence consisting of SEQ ID NO:1.

In one embodiment, the nucleic acid molecule comprises a nucleotide sequence having at least about 95% identity over an entire length of the nucleic acid sequence of SEQ ID NO:3, SEQ ID NO:5, SEQ ID NO:7, SEQ ID NO:9 or SEQ ID NO:11.

In one embodiment, the nucleotide sequence encodes a leader sequence.

In one embodiment, the nucleic acid molecule is an expression vector.

In one embodiment, the invention relates to a composition comprising at least one nucleic acid molecule encoding one or more synthetic antibodies or fragment thereof, wherein the nucleic acid molecule comprises a nucleotide sequence encoding a synthetic antibody or a nucleotide sequence encoding a fragment of a synthetic antibody. In one embodiment, the one or more synthetic antibodies is a monoclonal antibody, monofunctional antibody, bifunctional antibody, bispecific antibody, multivalent antibody, defucosylated antibody, non-fucosylated antibody, an immunoglobulin, or any combination thereof. In one embodiment, the composition comprises at least one nucleic acid molecule encoding a fragment of a multivalent antibody. In one embodiment, the multivalent antibody is a hexameric antibody that forms in vivo. In one embodiment, the nucleic acid molecule encodes a heavy chain of a multivalent antibody comprising a variation of at least one Fc residue of Q311, A339, E430, E345, D356, I253, S254, Y436, Q386, E382, or S440. In one embodiment, the nucleic acid molecule encodes a heavy chain of a multivalent antibody comprising a variation of at least one Fc residue of E345K, E430G, or S440Y.

In one embodiment, the composition comprises at least one nucleic acid molecule encoding one or more synthetic antibodies, or fragments thereof, wherein the nucleic acid molecule comprises a nucleotide sequence encoding an anti-*Neisseria gonorrhoeae* synthetic antibody. In one embodiment, the nucleic acid molecule encodes one or more synthetic antibodies, or fragments thereof, wherein the nucleic acid molecule comprises a nucleotide sequence encoding a fragment of an anti-*Neisseria gonorrhoeae* synthetic antibody. In one embodiment, the nucleic acid molecule encodes one or more synthetic antibodies, or fragments thereof, wherein the nucleic acid molecule comprises a variant of nucleotide sequence encoding an anti-*Neisseria gonorrhoeae* synthetic antibody. In one embodiment, the nucleic acid molecule encodes one or more synthetic antibodies, or fragments thereof, wherein the nucleic acid molecule comprises a variant of a nucleotide sequence encoding a fragment of an anti-*Neisseria gonorrhoeae* synthetic antibody.

In one embodiment, the composition comprises at least one nucleic acid molecule encoding a light chain of an anti-*Neisseria gonorrhoeae* antibody. In one embodiment, the composition comprises at least one nucleic acid molecule encoding a heavy chain of an anti-*Neisseria gonorrhoeae* antibody.

In one embodiment, the composition comprises at least one nucleic acid molecule comprising a nucleotide sequence encoding an amino acid sequence having at least about 95% identity over an entire length of the amino acid sequence SEQ ID NO:2.

In one embodiment, the composition comprises at least one nucleic acid molecule comprising a nucleotide sequence encoding an amino acid sequence having at least about 95% identity over an entire length of the amino acid sequence of SEQ ID NO:4, SEQ ID NO:6, SEQ ID NO:8, SEQ ID NO:10, or SEQ ID NO:12.

In one embodiment, the composition comprises at least one nucleic acid molecule comprising a nucleotide sequence having at least about 95% identity over an entire length of the nucleic acid sequence consisting of SEQ ID NO:1.

In one embodiment, the composition comprises at least one nucleic acid molecule comprising a nucleotide sequence having at least about 95% identity over an entire length of the nucleic acid sequence of SEQ ID NO:3, SEQ ID NO:5, SEQ ID NO:7, SEQ ID NO:9, or SEQ ID NO:11.

In one embodiment, the composition comprises at least one nucleic acid molecule comprising a nucleotide sequence encoding a leader sequence.

In one embodiment, the composition comprises at least one expression vector.

In one embodiment, the composition comprises at least one nucleic acid molecule comprising a nucleotide sequence encoding an amino acid sequence having at least about 95% identity over an entire length of the amino acid sequence SEQ ID NO:2, and at least one nucleic acid molecule comprising a nucleotide sequence encoding an amino acid sequence having at least about 95% identity over an entire length of the amino acid sequence of SEQ ID NO:4, SEQ ID NO:6, SEQ ID NO:8, SEQ ID NO:10, or SEQ ID NO:12.

In one embodiment, the composition comprises at least one nucleic acid molecule comprising a nucleotide sequence having at least about 95% identity over an entire length of the nucleic acid sequence consisting of SEQ ID NO:1, and at least one nucleic acid molecule comprising a nucleotide sequence having at least about 95% identity over an entire length of the nucleic acid sequence of SEQ ID NO:3, SEQ ID NO:5, SEQ ID NO:7, SEQ ID NO:9, or SEQ ID NO:11.

In one embodiment, the composition comprises a pharmaceutically acceptable excipient.

In one embodiment, the invention relates to a method of treating a disease or disorder in a subject, the method comprising administering to the subject a nucleic acid molecule, or a composition comprising a nucleic acid molecule, encoding one or more synthetic antibodies or fragment thereof, wherein the nucleic acid molecule comprises a nucleotide sequence encoding a synthetic antibody or a nucleotide sequence encoding a fragment of a synthetic antibody. In one embodiment, the one or more synthetic antibodies is a monoclonal antibody, monofunctional antibody, bifunctional antibody, bispecific antibody, multivalent antibody, defucosylated antibody, non-fucosylated antibody, an immunoglobulin, or any combination thereof.

In one embodiment, the nucleic acid molecule encodes a fragment of a multivalent antibody. In one embodiment, the multivalent antibody is a hexameric antibody that forms in vivo. In one embodiment, the nucleic acid molecule encodes a heavy chain of a multivalent antibody comprising a variation of at least one Fc residue of Q311, A339, E430, E345, D356, I253, S254, Y436, Q386, E382, or S440. In one embodiment, the nucleic acid molecule encodes a heavy chain of a multivalent antibody comprising a variation of at least one Fc residue of E345K, E430G, or S440Y.

In one embodiment, the disease or disorder is a bacterial infection, a viral infection, a fungal infection, a disease or disorder associated with a parasite, or cancer. In one embodiment, the disease is a *Neisseria gonorrhoeae* infection.

In one embodiment, the invention relates to a method of inducing an immune response in a subject, the method comprising administering to the subject a nucleic acid molecule, or a composition comprising a nucleic acid molecule, encoding one or more synthetic antibodies or fragment thereof, wherein the nucleic acid molecule comprises a nucleotide sequence encoding a synthetic antibody or a nucleotide sequence encoding a fragment of a synthetic antibody. In one embodiment, the one or more synthetic antibodies is a monoclonal antibody, monofunctional antibody, bifunctional antibody, bispecific antibody, multivalent antibody, defucosylated antibody, non-fucosylated antibody, an immunoglobulin, or any combination thereof.

In one embodiment, the nucleic acid molecule encodes a fragment of a multivalent antibody. In one embodiment, the multivalent antibody is a hexameric antibody that forms in vivo. In one embodiment, the nucleic acid molecule encodes a heavy chain of a multivalent antibody comprising a variation of at least one Fc residue of Q311, A339, E430, E345, D356, I253, S254, Y436, Q386, E382, or S440. In one embodiment, the nucleic acid molecule encodes a heavy chain of a multivalent antibody comprising a variation of at least one Fc residue of E345K, E430G, or S440Y.

BRIEF DESCRIPTION OF THE DRAWINGS

FIG. 4 depicts exemplary experimental results demonstrating the bactericidal activity in serum from 2C7 DMAb-administered mice.

DETAILED DESCRIPTION

Figure 1:
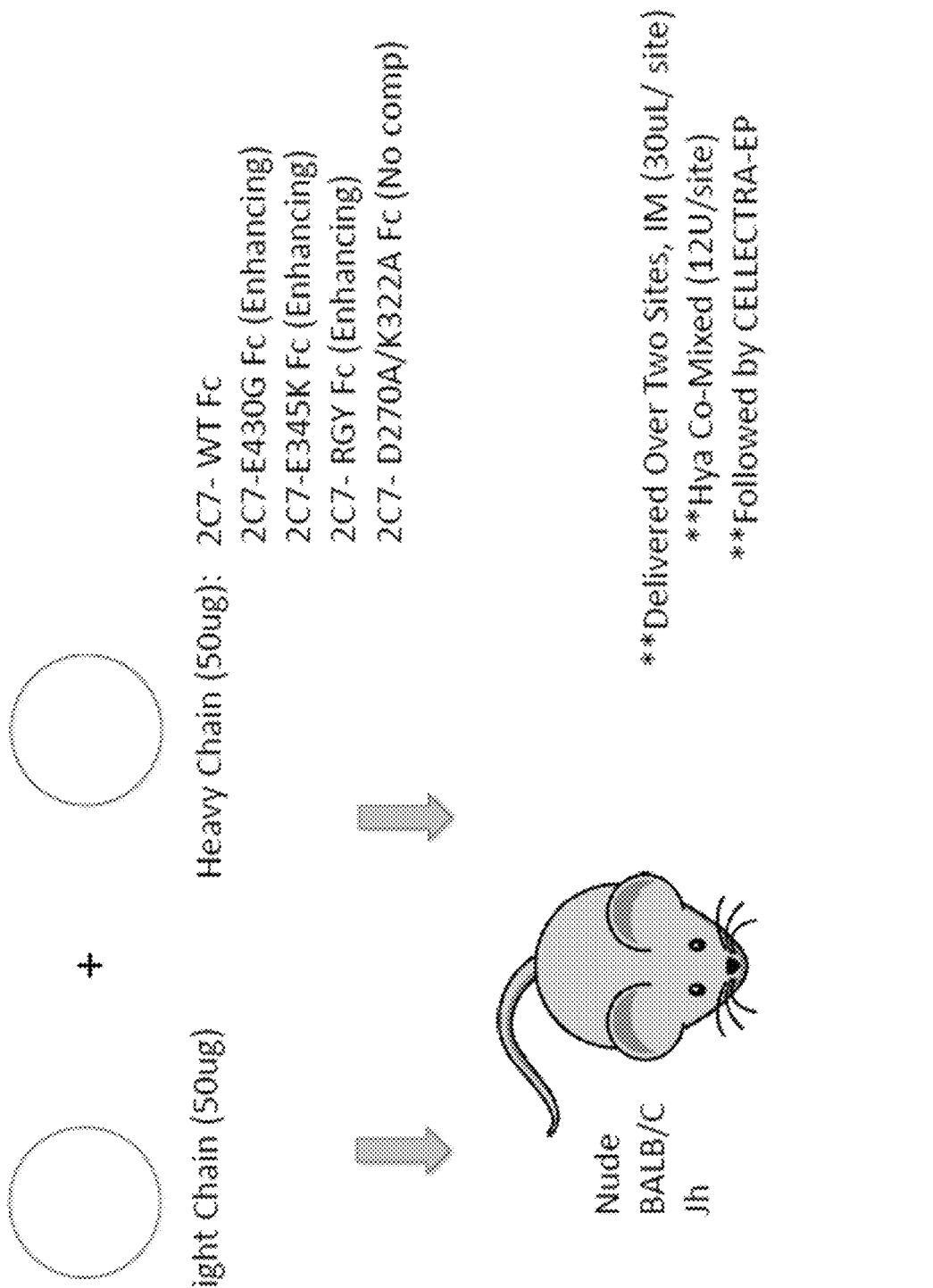
FIG. 1 depicts a schematic diagram of the 2C7-based DMAb construct design.

The present invention relates to compositions comprising a recombinant nucleic acid sequence encoding an antibody, a fragment thereof, a variant thereof, or a combination thereof. The composition can be administered to a subject in need thereof to facilitate in vivo expression and formation of a synthetic antibody.

In particular, the heavy chain and light chain polypeptides expressed from the recombinant nucleic acid sequences can assemble into the synthetic antibody. The heavy chain polypeptide and the light chain polypeptide can interact with one another such that assembly results in the synthetic antibody being capable of binding the antigen, being more immunogenic as compared to an antibody not assembled as described herein, and being capable of eliciting or inducing an immune response against the antigen.

Additionally, these synthetic antibodies are generated more rapidly in the subject than antibodies that are produced in response to antigen induced immune response. The synthetic antibodies are able to effectively bind and neutralize a range of antigens. The synthetic antibodies are also able to effectively protect against and/or promote survival of disease.

A sequence listing provided herein contains 10 sequences including the following:

SEQ ID NO: 1 is the nucleotide sequence of the light chain of the 2C7 DMAb.

SEQ ID NO: 2 is the amino acid sequence of the light chain of the 2C7 DMAb.

SEQ ID NO: 3 is the nucleotide sequence of the heavy chain of the 2C7 DMAb.

SEQ ID NO: 4 is the amino acid sequence of the heavy chain of the 2C7 DMAb.

SEQ ID NO: 5 is the nucleotide sequence of the heavy chain of the E430G 2C7 DMAb.

SEQ ID NO: 6 is the amino acid sequence of the heavy chain of the E430G 2C7 DMAb.

SEQ ID NO: 7 is the nucleotide sequence of the heavy chain of the E345K 2C7 DMAb.

SEQ ID NO: 8 is the amino acid sequence of the heavy chain of the E345K 2C7 DMAb.

SEQ ID NO: 9 is the nucleotide sequence of the heavy chain of the RGY 2C7 DMAb.

SEQ ID NO: 10 is the amino acid sequence of the heavy chain of the RGY 2C7 DMAb.

SEQ ID NO: 11 is the nucleotide sequence of the heavy chain of the NOCOMP 2C7 DMAb.

SEQ ID NO: 12 is the amino acid sequence of the heavy chain of the NOCOMP 2C7 DMAb.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

"Antibody" may mean an antibody of classes IgG, IgM, IgA, IgD or IgE, or fragments, fragments or derivatives thereof, including Fab, F(ab')2, Fd, and single chain antibodies, and derivatives thereof. The antibody may be an antibody isolated from the serum sample of mammal, a polyclonal antibody, affinity purified antibody, or mixtures thereof which exhibits sufficient binding specificity to a desired epitope or a sequence derived therefrom.

"Antibody fragment" or "fragment of an antibody" as used interchangeably herein refers to a portion of an intact antibody comprising the antigen-binding site or variable region. The portion may include the constant heavy chain domains (i.e. CH2, CH3, or CH4, depending on the antibody isotype) of the Fc region of the intact antibody. Examples of antibody fragments include, but are not limited to, Fab fragments, Fab' fragments, Fab'-SH fragments, F(ab')2 fragments, Fd fragments, Fv fragments, diabodies, single-chain Fv (scFv) molecules, single-chain polypeptides containing only one light chain variable domain, single-chain polypeptides containing the three CDRs of the light-chain variable domain, single-chain polypeptides containing only one heavy chain variable region, and single-chain polypeptides containing the three CDRs of the heavy chain variable region.

"Antigen" refers to proteins that have the ability to generate an immune response in a host. An antigen may be recognized and bound by an antibody. An antigen may originate from within the body or from the external environment.

As used herein, the term "2C7 antigen" or "2C7 epitope" refers to a highly conserved oligosaccharide structure, a part of lipooligosaccharide (LOS), on *Neisseria gonorrhoeae*. LOS is a critical component of the outer membrane of *Neisseria gonorrhoeae*. The 2C7 epitope is expressed by 94% of gonococci in the human genital tract. The structure of the 2C7 epitope requires substitution of lactose on Heptose I and II of the LOS structure (Gulati, S., et al., PLoS Pathogens 2013 e1003559). The 2C7 epitope is critical for gonococcal infection and antibodies against the 2C7 epitope are known to cause bacterial killing (Gulati, S., et al., PLoS Pathogens 2013 e1003559). The anti-2C7 antibodies disclosed herein have binding specificity for the 2C7 epitope.

"Coding sequence" or "encoding nucleic acid" as used herein may mean refers to the nucleic acid (RNA or DNA molecule) that comprise a nucleotide sequence which encodes an antibody as set forth herein. The coding sequence may further include initiation and termination signals operably linked to regulatory elements including a promoter and polyadenylation signal capable of directing expression in the cells of an individual or mammal to whom the nucleic acid is administered. The coding sequence may further include sequences that encode signal peptides.

"Complement" or "complementary" as used herein may mean a nucleic acid may mean Watson-Crick (e.g., A-T/U and C-G) or Hoogsteen base pairing between nucleotides or nucleotide analogs of nucleic acid molecules.

"Constant current" as used herein to define a current that is received or experienced by a tissue, or cells defining said tissue, over the duration of an electrical pulse delivered to same tissue. The electrical pulse is delivered from the electroporation devices described herein. This current remains at a constant amperage in said tissue over the life of an electrical pulse because the electroporation device provided herein has a feedback element, preferably having instantaneous feedback. The feedback element can measure the resistance of the tissue (or cells) throughout the duration of the pulse and cause the electroporation device to alter its electrical energy output (e.g., increase voltage) so current in same tissue remains constant throughout the electrical pulse (on the order of microseconds), and from pulse to pulse. In some embodiments, the feedback element comprises a controller.

"Current feedback" or "feedback" as used herein may be used interchangeably and may mean the active response of the provided electroporation devices, which comprises measuring the current in tissue between electrodes and altering the energy output delivered by the EP device accordingly in order to maintain the current at a constant level. This constant level is preset by a user prior to initiation of a pulse sequence or electrical treatment. The feedback may be accomplished by the electroporation component, e.g., controller, of the electroporation device, as the electrical circuit therein is able to continuously monitor the current in tissue between electrodes and compare that monitored current (or current within tissue) to a preset current and continuously make energy-output adjustments to maintain the monitored current at preset levels. The feedback loop may be instantaneous as it is an analog closed-loop feedback.

"Decentralized current" as used herein may mean the pattern of electrical currents delivered from the various needle electrode arrays of the electroporation devices described herein, wherein the patterns minimize, or preferably eliminate, the occurrence of electroporation related heat stress on any area of tissue being electroporated.

"Electroporation," "electro-permeabilization," or "electro-kinetic enhancement" ("EP") as used interchangeably herein may refer to the use of a transmembrane electric field pulse to induce microscopic pathways (pores) in a biomembrane; their presence allows biomolecules such as plasmids, oligonucleotides, siRNA, drugs, ions, and water to pass from one side of the cellular membrane to the other.

"Endogenous antibody" as used herein may refer to an antibody that is generated in a subject that is administered an effective dose of an antigen for induction of a humoral immune response.

"Feedback mechanism" as used herein may refer to a process performed by either software or hardware (or firmware), which process receives and compares the impedance of the desired tissue (before, during, and/or after the delivery of pulse of energy) with a present value, preferably current, and adjusts the pulse of energy delivered to achieve the preset value. A feedback mechanism may be performed by an analog closed loop circuit.

"Fragment" may mean a polypeptide fragment of an antibody that is function, i.e., can bind to desired target and have the same intended effect as a full length antibody. A fragment of an antibody may be 100% identical to the full length except missing at least one amino acid from the N and/or C terminal, in each case with or without signal peptides and/or a methionine at position 1. Fragments may comprise 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, 91% or more, 92% or more, 93% or more, 94% or more, 95% or more, 96% or more, 97% or more, 98% or more, 99% or more percent of the length of the particular full length antibody, excluding any heterologous signal peptide added. The fragment may comprise a fragment of a polypeptide that is 95% or more, 96% or more, 97% or more, 98% or more or 99% or more identical to the antibody and additionally comprise an N terminal methionine or heterologous signal peptide which is not included when calculating percent identity. Fragments may further comprise an N terminal methionine and/or a signal peptide such as an immunoglobulin signal peptide, for example an IgE or IgG signal peptide. The N terminal methionine and/or signal peptide may be linked to a fragment of an antibody.

A fragment of a nucleic acid sequence that encodes an antibody may be 100% identical to the full length except missing at least one nucleotide from the 5' and/or 3' end, in each case with or without sequences encoding signal peptides and/or a methionine at position 1. Fragments may comprise 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, 91% or more, 92% or more, 93% or more, 94% or more, 95% or more, 96% or more, 97% or more, 98% or more, 99% or more percent of the length of the particular full length coding sequence, excluding any heterologous signal peptide added. The fragment may comprise a fragment that encode a polypeptide that is 95% or more, 96% or more, 97% or more, 98% or more or 99% or more identical to the antibody and additionally optionally comprise sequence encoding an N terminal methionine or heterologous signal peptide which is not included when calculating percent identity. Fragments may further comprise coding sequences for an N terminal methionine and/or a signal peptide such as an immunoglobulin signal peptide, for example an IgE or IgG signal peptide. The coding sequence encoding the N terminal methionine and/or signal peptide may be linked to a fragment of coding sequence.

"Genetic construct" as used herein refers to the DNA or RNA molecules that comprise a nucleotide sequence which encodes a protein, such as an antibody. The coding sequence includes initiation and termination signals operably linked to regulatory elements including a promoter and polyadenylation signal capable of directing expression in the cells of the individual to whom the nucleic acid molecule is administered. As used herein, the term "expressible form" refers to gene constructs that contain the necessary regulatory elements operable linked to a coding sequence that encodes a protein such that when present in the cell of the individual, the coding sequence will be expressed.

"Identical" or "identity" as used herein in the context of two or more nucleic acids or polypeptide sequences, may mean that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) may be considered equivalent. Identity may be performed manually or by using a computer sequence algorithm such as BLAST or BLAST 2.0.

"Impedance" as used herein may be used when discussing the feedback mechanism and can be converted to a current value according to Ohm's law, thus enabling comparisons with the preset current.

"Immune response" as used herein may mean the activation of a host's immune system, e.g., that of a mammal, in response to the introduction of one or more nucleic acids and/or peptides. The immune response can be in the form of a cellular or humoral response, or both.

"Nucleic acid" or "oligonucleotide" or "polynucleotide" as used herein may mean at least two nucleotides covalently linked together. The depiction of a single strand also defines the sequence of the complementary strand. Thus, a nucleic acid also encompasses the complementary strand of a depicted single strand. Many variants of a nucleic acid may be used for the same purpose as a given nucleic acid. Thus, a nucleic acid also encompasses substantially identical nucleic acids and complements thereof. A single strand provides a probe that may hybridize to a target sequence under stringent hybridization conditions. Thus, a nucleic acid also encompasses a probe that hybridizes under stringent hybridization conditions.

Nucleic acids may be single stranded or double stranded, or may contain portions of both double stranded and single stranded sequence. The nucleic acid may be DNA, both genomic and cDNA, RNA, or a hybrid, where the nucleic acid may contain combinations of deoxyribo- and ribonucleotides, and combinations of bases including uracil, adenine, thymine, cytosine, guanine, inosine, xanthine hypoxanthine, isocytosine and isoguanine. Nucleic acids may be obtained by chemical synthesis methods or by recombinant methods.

"Operably linked" as used herein may mean that expression of a gene is under the control of a promoter with which it is spatially connected. A promoter may be positioned 5' (upstream) or 3' (downstream) of a gene under its control. The distance between the promoter and a gene may be approximately the same as the distance between that promoter and the gene it controls in the gene from which the promoter is derived. As is known in the art, variation in this distance may be accommodated without loss of promoter function.

A "peptide," "protein," or "polypeptide" as used herein can mean a linked sequence of amino acids and can be natural, synthetic, or a modification or combination of natural and synthetic.

"Promoter" as used herein may mean a synthetic or naturally-derived molecule which is capable of conferring, activating or enhancing expression of a nucleic acid in a cell. A promoter may comprise one or more specific transcriptional regulatory sequences to further enhance expression and/or to alter the spatial expression and/or temporal expression of same. A promoter may also comprise distal enhancer or repressor elements, which can be located as much as several thousand base pairs from the start site of transcription. A promoter may be derived from sources including viral, bacterial, fungal, plants, insects, and animals. A promoter may regulate the expression of a gene component constitutively, or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV 40 late promoter and the CMV IE promoter.

"Signal peptide" and "leader sequence" are used interchangeably herein and refer to an amino acid sequence that can be linked at the amino terminus of a protein set forth herein. Signal peptides/leader sequences typically direct localization of a protein. Signal peptides/leader sequences used herein preferably facilitate secretion of the protein from the cell in which it is produced. Signal peptides/leader sequences are often cleaved from the remainder of the protein, often referred to as the mature protein, upon secretion from the cell. Signal peptides/leader sequences are linked at the N terminus of the protein.

"Stringent hybridization conditions" as used herein may mean conditions under which a first nucleic acid sequence (e.g., probe) will hybridize to a second nucleic acid sequence (e.g., target), such as in a complex mixture of nucleic acids. Stringent conditions are sequence dependent and will be different in different circumstances. Stringent conditions may be selected to be about 5-10° C. lower than the thermal melting point ($T_m$) for the specific sequence at a defined ionic strength pH. The $T_m$ may be the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions may also be achieved with the addition of destabilizing agents such as formamide. For selective or specific hybridization, a positive signal may be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.

"Subject" and "patient" as used herein interchangeably refers to any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgous or rhesus monkey, chimpanzee, etc) and a human). In some embodiments, the subject may be a human or a non-human. The subject or patient may be undergoing other forms of treatment.

"Substantially complementary" as used herein may mean that a first sequence is at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleotides or amino acids, or that the two sequences hybridize under stringent hybridization conditions.

"Substantially identical" as used herein may mean that a first and second sequence are at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% over a region of 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 200, 300, 400, 500, 600, 700, 800, 900, 1000, 1100 or more nucleotides or amino acids, or with respect to nucleic acids, if the first sequence is substantially complementary to the complement of the second sequence.

"Synthetic antibody" as used herein refers to an antibody that is encoded by the recombinant nucleic acid sequence described herein and is generated in a subject.

"Treatment" or "treating," as used herein can mean protecting of a subject from a disease through means of preventing, suppressing, repressing, or completely eliminating the disease. Preventing the disease involves administering a vaccine of the present invention to a subject prior to onset of the disease. Suppressing the disease involves administering a composition of the present invention to a subject after induction of the disease but before its clinical appearance. Repressing the disease involves administering a composition of the present invention to a subject after clinical appearance of the disease.

"Variant" used herein with respect to a nucleic acid may mean (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

"Variant" with respect to a peptide or polypeptide that differs in amino acid sequence by the insertion, deletion, or conservative substitution of amino acids, but retain at least one biological activity. Variant may also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., J. Mol. Biol. 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, incorporated fully herein by reference. Substitution of amino acids having similar hydrophilicity values can result in peptides retaining biological activity, for example immunogenicity, as is understood in the art. Substitutions may be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

A variant may be a nucleic acid sequence that is substantially identical over the full length of the full gene sequence or a fragment thereof. The nucleic acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the gene sequence or a fragment thereof. A variant may be an amino acid sequence that is substantially identical over the full length of the amino acid sequence or fragment thereof. The amino acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the amino acid sequence or a fragment thereof.

"Vector" as used herein may mean a nucleic acid sequence containing an origin of replication. A vector may be a plasmid, bacteriophage, bacterial artificial chromosome or yeast artificial chromosome. A vector may be a DNA or RNA vector. A vector may be either a self-replicating extrachromosomal vector or a vector which integrates into a host genome.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

2. Compositions

The present invention relates to a composition comprising a recombinant nucleic acid sequence encoding an antibody, a fragment thereof, a variant thereof, or a combination thereof. In some embodiments, the antibody is a monoclonal antibody, monofunctional antibody, bifunctional antibody, bispecific antibody, multivalent antibody, defucosylated antibody, non-fucosylated antibody, immunoglobulin, or any combination thereof. The composition, when administered to a subject in need thereof, can result in the generation of a synthetic antibody, or a synthetic a multivalent antibody, in the subject. The synthetic antibody can bind a target molecule (i.e., an antigen) present in the subject. Such binding can neutralize the antigen, block recognition of the antigen by another molecule, for example, a protein or nucleic acid, and elicit or induce an immune response to the antigen.

In one embodiment, the composition comprises a nucleotide sequence encoding a synthetic antibody. In one embodiment, the composition comprises a nucleic acid molecule comprising a first nucleotide sequence encoding a first synthetic antibody and a second nucleotide sequence encoding a second synthetic antibody. In one embodiment, the nucleic acid molecule comprises a nucleotide sequence encoding a cleavage domain.

In one embodiment, the composition comprises a nucleotide sequence encoding a fragment of a synthetic multivalent antibody. In one embodiment, multivalent antibody forms in vivo after expression of the nucleotide sequence. In one embodiment, multivalent antibody has a modified (e.g., increased or decreased) level of complement activation with respect to a parental non-multivalent antibody. In one embodiment, the multivalent antibody is a trimeric antibody, a tetrameric antibody, a pentameric antibody, or a hexameric antibody. Therefore, in one embodiment, the invention provides nucleic acid molecules comprising a nucleotide sequence encoding a multivalent antibody or a fragment thereof.

In one embodiment, the multivalent antibody is a hexameric antibody that forms in vivo. In one embodiment, the hexameric antibody of the invention comprises at least one Fc mutation to enhance Fc:Fc interaction and therefore promote hexamer formation. In one embodiment, the hexameric antibody of the invention comprises at least one Fc mutation of one or more of residues Q311, A339, E430, E345, D356, I253, S254, Y436, Q386, E382, and S440. In one embodiment, the composition comprises a nucleotide sequence encoding a fragment of a multivalent antibody comprising at least one of Fc mutation of E345K, E345R, E430G or S440Y.

The multivalent antibody of the invention may be specific for any target or antigen, including, but not limited to a bacterial antigen, a viral antigen, and a self-antigen. In one embodiment, the multivalent antibody of the invention can be used to treat, prevent and/or protect against any disease, disorder, or condition associated with the target or antigen to which the multivalent antibody specifically binds, including, but not limited to, bacterial infection, viral infection and cancer.

In one embodiment, the nucleic acid molecule comprises a nucleotide sequence encoding an anti-*Neisseria gonorrhoeae* antibody. In one embodiment, the nucleotide sequence encoding an anti-*Neisseria gonorrhoeae* antibody comprises one or more codon optimized nucleic acid sequences encoding an amino acid sequence as set forth in SEQ ID NO:2, SEQ ID NO:4, SEQ ID NO:6, SEQ ID NO:8, SEQ ID NO:10, or SEQ ID NO:12, or a fragment or variant thereof. In one embodiment, the nucleotide sequence encoding an anti-*Neisseria gonorrhoeae* antibody comprises one or more codon optimized nucleic acid sequences as set forth in SEQ ID NO:1, SEQ ID NO:3, SEQ ID NO:5, SEQ ID NO:7, SEQ ID NO:9, or SEQ ID NO:11, or a fragment or variant thereof.

The composition of the invention can treat, prevent and/or protect against any disease, disorder, or condition associated with *Neisseria gonorrhoeae* infection. In certain embodiments, the composition can treat, prevent, and or/protect against *Neisseria gonorrhoeae* bacterial infection. In certain embodiments, the composition can treat, prevent, and or/protect against condition associated with *Neisseria gonorrhoeae* infection.

The composition can result in the generation of the synthetic antibody in the subject within at least about 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 20 hours, 25 hours, 30 hours, 35 hours, 40 hours, 45 hours, 50 hours, or 60 hours of administration of the composition to the subject. The composition can result in generation of the synthetic antibody in the subject within at least about 1 day, 2 days, 3 days, 4 days, 5 days, 6 days, 7 days, 8 days, 9 days, or 10 days of administration of the composition to the subject. The composition can result in generation of the synthetic antibody in the subject within about 1 hour to about 6 days, about 1 hour to about 5 days, about 1 hour to about 4 days, about 1 hour to about 3 days, about 1 hour to about 2 days, about 1 hour to about 1 day, about 1 hour to about 72 hours, about 1 hour to about 60 hours, about 1 hour to about 48 hours, about 1 hour to about 36 hours, about 1 hour to about 24 hours, about 1 hour to about 12 hours, or about 1 hour to about 6 hours of administration of the composition to the subject.

The composition, when administered to the subject in need thereof, can result in the generation of the synthetic antibody in the subject more quickly than the generation of an endogenous antibody in a subject who is administered an antigen to induce a humoral immune response. The composition can result in the generation of the synthetic antibody at least about 1 day, 2 days, 3 days, 4 days, 5 days, 6 days, 7 days, 8 days, 9 days, or 10 days before the generation of the endogenous antibody in the subject who was administered an antigen to induce a humoral immune response.

The composition of the present invention can have features required of effective compositions such as being safe so that the composition does not cause illness or death; being protective against illness; and providing ease of administration, few side effects, biological stability and low cost per dose.

3. Recombinant Nucleic Acid Sequence

As described above, the composition can comprise a recombinant nucleic acid sequence. The recombinant nucleic acid sequence can encode the antibody, a fragment thereof, a variant thereof, or a combination thereof. The antibody is described in more detail below.

The recombinant nucleic acid sequence can be a heterologous nucleic acid sequence. The recombinant nucleic acid sequence can include one or more heterologous nucleic acid sequences.

The recombinant nucleic acid sequence can be an optimized nucleic acid sequence. Such optimization can increase or alter the immunogenicity of the antibody. Optimization can also improve transcription and/or translation. Optimization can include one or more of the following: low GC content leader sequence to increase transcription; mRNA stability and codon optimization; addition of a kozak sequence (e.g., GCCACC) for increased translation; addition of an immunoglobulin (Ig) leader sequence encoding a signal peptide; addition of an internal IRES sequence and eliminating to the extent possible cis-acting sequence motifs (i.e., internal TATA boxes).

a. Recombinant Nucleic Acid Sequence Construct

The recombinant nucleic acid sequence can include one or more recombinant nucleic acid sequence constructs. The recombinant nucleic acid sequence construct can include one or more components, which are described in more detail below.

The recombinant nucleic acid sequence construct can include a heterologous nucleic acid sequence that encodes a heavy chain polypeptide, a fragment thereof, a variant thereof, or a combination thereof. The recombinant nucleic acid sequence construct can include a heterologous nucleic acid sequence that encodes a light chain polypeptide, a fragment thereof, a variant thereof, or a combination thereof. The recombinant nucleic acid sequence construct can also include a heterologous nucleic acid sequence that encodes a protease or peptidase cleavage site. The recombinant nucleic acid sequence construct can also include a heterologous nucleic acid sequence that encodes an internal ribosome entry site (IRES). An IRES may be either a viral IRES or an eukaryotic IRES. The recombinant nucleic acid sequence construct can include one or more leader sequences, in which each leader sequence encodes a signal peptide. The recombinant nucleic acid sequence construct can include one or more promoters, one or more introns, one or more transcription termination regions, one or more initiation codons, one or more termination or stop codons, and/or one or more polyadenylation signals. The recombinant nucleic acid sequence construct can also include one or more linker or tag sequences. The tag sequence can encode a hemagglutinin (HA) tag.

(1) Heavy Chain Polypeptide

The recombinant nucleic acid sequence construct can include the heterologous nucleic acid encoding the heavy chain polypeptide, a fragment thereof, a variant thereof, or a combination thereof. The heavy chain polypeptide can include a variable heavy chain (VH) region and/or at least one constant heavy chain (CH) region. The at least one constant heavy chain region can include a constant heavy chain region 1 (CH1), a constant heavy chain region 2 (CH2), and a constant heavy chain region 3 (CH3), and/or a hinge region.

In some embodiments, the heavy chain polypeptide can include a VH region and a CH1 region. In other embodiments, the heavy chain polypeptide can include a VH region, a CH1 region, a hinge region, a CH2 region, and a CH3 region.

The heavy chain polypeptide can include a complementarity determining region ("CDR") set. The CDR set can contain three hypervariable regions of the VH region. Proceeding from N-terminus of the heavy chain polypeptide, these CDRs are denoted "CDR1," "CDR2," and "CDR3," respectively. CDR1, CDR2, and CDR3 of the heavy chain polypeptide can contribute to binding or recognition of the antigen.

(2) Light Chain Polypeptide

The recombinant nucleic acid sequence construct can include the heterologous nucleic acid sequence encoding the light chain polypeptide, a fragment thereof, a variant thereof, or a combination thereof. The light chain polypeptide can include a variable light chain (VL) region and/or a constant light chain (CL) region.

The light chain polypeptide can include a complementarity determining region ("CDR") set. The CDR set can contain three hypervariable regions of the VL region. Proceeding from N-terminus of the light chain polypeptide, these CDRs are denoted "CDR1," "CDR2," and "CDR3,"

respectively. CDR1, CDR2, and CDR3 of the light chain polypeptide can contribute to binding or recognition of the antigen.

(3) Protease Cleavage Site

The recombinant nucleic acid sequence construct can include heterologous nucleic acid sequence encoding a protease cleavage site. The protease cleavage site can be recognized by a protease or peptidase. The protease can be an endopeptidase or endoprotease, for example, but not limited to, furin, elastase, HtrA, calpain, trypsin, chymotrypsin, trypsin, and pepsin. The protease can be furin. In other embodiments, the protease can be a serine protease, a threonine protease, cysteine protease, aspartate protease, metalloprotease, glutamic acid protease, or any protease that cleaves an internal peptide bond (i.e., does not cleave the N-terminal or C-terminal peptide bond).

The protease cleavage site can include one or more amino acid sequences that promote or increase the efficiency of cleavage. The one or more amino acid sequences can promote or increase the efficiency of forming or generating discrete polypeptides. The one or more amino acids sequences can include a 2A peptide sequence.

(4) Linker Sequence

The recombinant nucleic acid sequence construct can include one or more linker sequences. The linker sequence can spatially separate or link the one or more components described herein. In other embodiments, the linker sequence can encode an amino acid sequence that spatially separates or links two or more polypeptides.

(5) Promoter

The recombinant nucleic acid sequence construct can include one or more promoters. The one or more promoters may be any promoter that is capable of driving gene expression and regulating gene expression. Such a promoter is a cis-acting sequence element required for transcription via a DNA dependent RNA polymerase. Selection of the promoter used to direct gene expression depends on the particular application. The promoter may be positioned about the same distance from the transcription start in the recombinant nucleic acid sequence construct as it is from the transcription start site in its natural setting. However, variation in this distance may be accommodated without loss of promoter function.

The promoter may be operably linked to the heterologous nucleic acid sequence encoding the heavy chain polypeptide and/or light chain polypeptide. The promoter may be a promoter shown effective for expression in eukaryotic cells. The promoter operably linked to the coding sequence may be a promoter from simian virus 40 (SV40), such as SV40 early promoter and SV40 later promoter, a mouse mammary tumor virus (MMTV) promoter, a cytomegalovirus (CMV) promoter such as the CMV immediate early promoter, Epstein Barr virus (EBV) promoter, or a Rous sarcoma virus (RSV) promoter. The promoter may also be a promoter from a human gene such as human actin, human myosin, human hemoglobin, human muscle creatine, human polyhedrin, or human metalothionein.

The promoter can be a constitutive promoter or an inducible promoter, which initiates transcription only when the host cell is exposed to some particular external stimulus. In the case of a multicellular organism, the promoter can also be specific to a particular tissue or organ or stage of development. The promoter may also be a tissue specific promoter, such as a muscle or skin specific promoter, natural or synthetic. Examples of such promoters are described in US patent application publication no. US20040175727, the contents of which are incorporated herein in its entirety.

The promoter can be associated with an enhancer. The enhancer can be located upstream of the coding sequence. The enhancer may be human actin, human myosin, human hemoglobin, human muscle creatine or a viral enhancer such as one from CMV, FMDV, RSV or EBV. Polynucleotide function enhances are described in U.S. Pat. Nos. 5,593,972, 5,962,428, and WO94/016737, the contents of each are fully incorporated by reference.

(6) Intron

The recombinant nucleic acid sequence construct can include one or more introns. Each intron can include functional splice donor and acceptor sites. The intron can include an enhancer of splicing. The intron can include one or more signals required for efficient splicing.

(7) Transcription Termination Region

The recombinant nucleic acid sequence construct can include one or more transcription termination regions. The transcription termination region can be downstream of the coding sequence to provide for efficient termination. The transcription termination region can be obtained from the same gene as the promoter described above or can be obtained from one or more different genes.

(8) Initiation Codon

The recombinant nucleic acid sequence construct can include one or more initiation codons. The initiation codon can be located upstream of the coding sequence. The initiation codon can be in frame with the coding sequence. The initiation codon can be associated with one or more signals required for efficient translation initiation, for example, but not limited to, a ribosome binding site.

(9) Termination Codon

The recombinant nucleic acid sequence construct can include one or more termination or stop codons. The termination codon can be downstream of the coding sequence. The termination codon can be in frame with the coding sequence. The termination codon can be associated with one or more signals required for efficient translation termination.

(10) Polyadenylation Signal

The recombinant nucleic acid sequence construct can include one or more polyadenylation signals. The polyadenylation signal can include one or more signals required for efficient polyadenylation of the transcript. The polyadenylation signal can be positioned downstream of the coding sequence. The polyadenylation signal may be a SV40 polyadenylation signal, LTR polyadenylation signal, bovine growth hormone (bGH) polyadenylation signal, human growth hormone (hGH) polyadenylation signal, or human β-globin polyadenylation signal. The SV40 polyadenylation signal may be a polyadenylation signal from a pCEP4 plasmid (Invitrogen, San Diego, Calif.).

(11) Leader Sequence

The recombinant nucleic acid sequence construct can include one or more leader sequences. The leader sequence can encode a signal peptide. The signal peptide can be an immunoglobulin (Ig) signal peptide, for example, but not limited to, an IgG signal peptide and a IgE signal peptide.

b. Arrangement of the Recombinant Nucleic Acid Sequence Construct

As described above, the recombinant nucleic acid sequence can include one or more recombinant nucleic acid sequence constructs, in which each recombinant nucleic acid sequence construct can include one or more components. The one or more components are described in detail above. The one or more components, when included in the recombinant nucleic acid sequence construct, can be arranged in any order relative to one another. In some embodiments, the one or more components can be arranged in the recombinant nucleic acid sequence construct as described below.

(1) Arrangement 1

In one arrangement, a first recombinant nucleic acid sequence construct can include the heterologous nucleic acid sequence encoding the heavy chain polypeptide and a second recombinant nucleic acid sequence construct can include the heterologous nucleic acid sequence encoding the light chain polypeptide.

The first recombinant nucleic acid sequence construct can be placed in a vector. The second recombinant nucleic acid sequence construct can be placed in a second or separate vector. Placement of the recombinant nucleic acid sequence construct into the vector is described in more detail below.

The first recombinant nucleic acid sequence construct can also include the promoter, intron, transcription termination region, initiation codon, termination codon, and/or polyadenylation signal. The first recombinant nucleic acid sequence construct can further include the leader sequence, in which the leader sequence is located upstream (or 5') of the heterologous nucleic acid sequence encoding the heavy chain polypeptide. Accordingly, the signal peptide encoded by the leader sequence can be linked by a peptide bond to the heavy chain polypeptide.

The second recombinant nucleic acid sequence construct can also include the promoter, initiation codon, termination codon, and polyadenylation signal. The second recombinant nucleic acid sequence construct can further include the leader sequence, in which the leader sequence is located upstream (or 5') of the heterologous nucleic acid sequence encoding the light chain polypeptide. Accordingly, the signal peptide encoded by the leader sequence can be linked by a peptide bond to the light chain polypeptide.

Accordingly, one example of arrangement 1 can include the first vector (and thus first recombinant nucleic acid sequence construct) encoding the heavy chain polypeptide that includes VH and CH1, and the second vector (and thus second recombinant nucleic acid sequence construct) encoding the light chain polypeptide that includes VL and CL. A second example of arrangement 1 can include the first vector (and thus first recombinant nucleic acid sequence construct) encoding the heavy chain polypeptide that includes VH, CH1, hinge region, CH2, and CH3, and the second vector (and thus second recombinant nucleic acid sequence construct) encoding the light chain polypeptide that includes VL and CL.

(2) Arrangement 2

In a second arrangement, the recombinant nucleic acid sequence construct can include the heterologous nucleic acid sequence encoding the heavy chain polypeptide and the heterologous nucleic acid sequence encoding the light chain polypeptide. The heterologous nucleic acid sequence encoding the heavy chain polypeptide can be positioned upstream (or 5') of the heterologous nucleic acid sequence encoding the light chain polypeptide. Alternatively, the heterologous nucleic acid sequence encoding the light chain polypeptide can be positioned upstream (or 5') of the heterologous nucleic acid sequence encoding the heavy chain polypeptide.

The recombinant nucleic acid sequence construct can be placed in the vector as described in more detail below.

The recombinant nucleic acid sequence construct can include the heterologous nucleic acid sequence encoding the protease cleavage site and/or the linker sequence. If included in the recombinant nucleic acid sequence construct, the heterologous nucleic acid sequence encoding the protease cleavage site can be positioned between the heterologous nucleic acid sequence encoding the heavy chain polypeptide and the heterologous nucleic acid sequence encoding the light chain polypeptide. Accordingly, the protease cleavage site allows for separation of the heavy chain polypeptide and the light chain polypeptide into distinct polypeptides upon expression. In other embodiments, if the linker sequence is included in the recombinant nucleic acid sequence construct, then the linker sequence can be positioned between the heterologous nucleic acid sequence encoding the heavy chain polypeptide and the heterologous nucleic acid sequence encoding the light chain polypeptide.

The recombinant nucleic acid sequence construct can also include the promoter, intron, transcription termination region, initiation codon, termination codon, and/or polyadenylation signal. The recombinant nucleic acid sequence construct can include one or more promoters. The recombinant nucleic acid sequence construct can include two promoters such that one promoter can be associated with the heterologous nucleic acid sequence encoding the heavy chain polypeptide and the second promoter can be associated with the heterologous nucleic acid sequence encoding the light chain polypeptide. In still other embodiments, the recombinant nucleic acid sequence construct can include one promoter that is associated with the heterologous nucleic acid sequence encoding the heavy chain polypeptide and the heterologous nucleic acid sequence encoding the light chain polypeptide.

The recombinant nucleic acid sequence construct can further include two leader sequences, in which a first leader sequence is located upstream (or 5') of the heterologous nucleic acid sequence encoding the heavy chain polypeptide and a second leader sequence is located upstream (or 5') of the heterologous nucleic acid sequence encoding the light chain polypeptide. Accordingly, a first signal peptide encoded by the first leader sequence can be linked by a peptide bond to the heavy chain polypeptide and a second signal peptide encoded by the second leader sequence can be linked by a peptide bond to the light chain polypeptide.

Accordingly, one example of arrangement 2 can include the vector (and thus recombinant nucleic acid sequence construct) encoding the heavy chain polypeptide that includes VH and CH1, and the light chain polypeptide that includes VL and CL, in which the linker sequence is positioned between the heterologous nucleic acid sequence encoding the heavy chain polypeptide and the heterologous nucleic acid sequence encoding the light chain polypeptide.

A second example of arrangement of 2 can include the vector (and thus recombinant nucleic acid sequence construct) encoding the heavy chain polypeptide that includes VH and CH1, and the light chain polypeptide that includes VL and CL, in which the heterologous nucleic acid sequence encoding the protease cleavage site is positioned between the heterologous nucleic acid sequence encoding the heavy chain polypeptide and the heterologous nucleic acid sequence encoding the light chain polypeptide.

A third example of arrangement 2 can include the vector (and thus recombinant nucleic acid sequence construct) encoding the heavy chain polypeptide that includes VH, CH1, hinge region, CH2, and CH3, and the light chain polypeptide that includes VL and CL, in which the linker sequence is positioned between the heterologous nucleic acid sequence encoding the heavy chain polypeptide and the heterologous nucleic acid sequence encoding the light chain polypeptide.

A forth example of arrangement of 2 can include the vector (and thus recombinant nucleic acid sequence construct) encoding the heavy chain polypeptide that includes VH, CH1, hinge region, CH2, and CH3, and the light chain polypeptide that includes VL and CL, in which the heterologous nucleic acid sequence encoding the protease cleavage site is positioned between the heterologous nucleic acid sequence encoding the heavy chain polypeptide and the heterologous nucleic acid sequence encoding the light chain polypeptide.

c. Expression from the Recombinant Nucleic Acid Sequence Construct

As described above, the recombinant nucleic acid sequence construct can include, amongst the one or more components, the heterologous nucleic acid sequence encoding the heavy chain polypeptide and/or the heterologous nucleic acid sequence encoding the light chain polypeptide. Accordingly, the recombinant nucleic acid sequence construct can facilitate expression of the heavy chain polypeptide and/or the light chain polypeptide.

When arrangement 1 as described above is utilized, the first recombinant nucleic acid sequence construct can facilitate the expression of the heavy chain polypeptide and the second recombinant nucleic acid sequence construct can facilitate expression of the light chain polypeptide. When arrangement 2 as described above is utilized, the recombinant nucleic acid sequence construct can facilitate the expression of the heavy chain polypeptide and the light chain polypeptide.

Upon expression, for example, but not limited to, in a cell, organism, or mammal, the heavy chain polypeptide and the light chain polypeptide can assemble into the synthetic antibody. In particular, the heavy chain polypeptide and the light chain polypeptide can interact with one another such that assembly results in the synthetic antibody being capable of binding the antigen. In other embodiments, the heavy chain polypeptide and the light chain polypeptide can interact with one another such that assembly results in the synthetic antibody being more immunogenic as compared to an antibody not assembled as described herein. In still other embodiments, the heavy chain polypeptide and the light chain polypeptide can interact with one another such that assembly results in the synthetic antibody being capable of eliciting or inducing an immune response against the antigen.

d. Vector

The recombinant nucleic acid sequence construct described above can be placed in one or more vectors. The one or more vectors can contain an origin of replication. The one or more vectors can be a plasmid, bacteriophage, bacterial artificial chromosome or yeast artificial chromosome. The one or more vectors can be either a self-replication extra chromosomal vector, or a vector which integrates into a host genome.

The one or more vectors can be a heterologous expression construct, which is generally a plasmid that is used to introduce a specific gene into a target cell. Once the expression vector is inside the cell, the heavy chain polypeptide and/or light chain polypeptide that are encoded by the recombinant nucleic acid sequence construct is produced by the cellular-transcription and translation machinery ribosomal complexes. The one or more vectors can express large amounts of stable messenger RNA, and therefore proteins.

(1) Expression Vector

The one or more vectors can be a circular plasmid or a linear nucleic acid. The circular plasmid and linear nucleic acid are capable of directing expression of a particular nucleotide sequence in an appropriate subject cell. The one or more vectors comprising the recombinant nucleic acid sequence construct may be chimeric, meaning that at least one of its components is heterologous with respect to at least one of its other components.

(2) Plasmid

The one or more vectors can be a plasmid. The plasmid may be useful for transfecting cells with the recombinant nucleic acid sequence construct. The plasmid may be useful for introducing the recombinant nucleic acid sequence construct into the subject. The plasmid may also comprise a regulatory sequence, which may be well suited for gene expression in a cell into which the plasmid is administered.

The plasmid may also comprise a mammalian origin of replication in order to maintain the plasmid extrachromosomally and produce multiple copies of the plasmid in a cell. The plasmid may be pVAX1, pCEP4 or pREP4 from Invitrogen (San Diego, CA), which may comprise the Epstein Barr virus origin of replication and nuclear antigen EBNA-1 coding region, which may produce high copy episomal replication without integration. The backbone of the plasmid may be pAV0242. The plasmid may be a replication defective adenovirus type 5 (Ad5) plasmid.

The plasmid may be pSE420 (Invitrogen, San Diego, Calif.), which may be used for protein production in *Escherichia coli* (*E. coli*). The plasmid may also be pYES2 (Invitrogen, San Diego, Calif.), which may be used for protein production in *Saccharomyces cerevisiae* strains of yeast. The plasmid may also be of the MAXBAC™ complete baculovirus expression system (Invitrogen, San Diego, Calif.), which may be used for protein production in insect cells. The plasmid may also be pcDNAI or pcDNA3 (Invitrogen, San Diego, Calif.), which may be used for protein production in mammalian cells such as Chinese hamster ovary (CHO) cells.

(3) Circular and Linear Vector

The one or more vectors may be circular plasmid, which may transform a target cell by integration into the cellular genome or exist extrachromosomally (e.g., autonomous replicating plasmid with an origin of replication). The vector can be pVAX, pcDNA3.0, or provax, or any other expression vector capable of expressing the heavy chain polypeptide and/or light chain polypeptide encoded by the recombinant nucleic acid sequence construct.

Also provided herein is a linear nucleic acid, or linear expression cassette ("LEC"), that is capable of being efficiently delivered to a subject via electroporation and expressing the heavy chain polypeptide and/or light chain polypeptide encoded by the recombinant nucleic acid sequence construct. The LEC may be any linear DNA devoid of any phosphate backbone. The LEC may not contain any antibiotic resistance genes and/or a phosphate backbone. The LEC may not contain other nucleic acid sequences unrelated to the desired gene expression.

The LEC may be derived from any plasmid capable of being linearized. The plasmid may be capable of expressing the heavy chain polypeptide and/or light chain polypeptide encoded by the recombinant nucleic acid sequence construct. The plasmid can be pNP (Puerto Rico/34) or pM2 (New Caledonia/99). The plasmid may be WLV009, pVAX, pcDNA3.0, or provax, or any other expression vector capable of expressing the heavy chain polypeptide and/or light chain polypeptide encoded by the recombinant nucleic acid sequence construct.

The LEC can be perM2. The LEC can be perNP. perNP and perMR can be derived from pNP (Puerto Rico/34) and pM2 (New Caledonia/99), respectively.

(4) Method of Preparing the Vector

Provided herein is a method for preparing the one or more vectors in which the recombinant nucleic acid sequence construct has been placed. After the final subcloning step, the vector can be used to inoculate a cell culture in a large scale fermentation tank, using known methods in the art.

In other embodiments, after the final subcloning step, the vector can be used with one or more electroporation (EP) devices. The EP devices are described below in more detail.

The one or more vectors can be formulated or manufactured using a combination of known devices and techniques, but preferably they are manufactured using a plasmid manufacturing technique that is described in a licensed, co-pending U.S. provisional application U.S. Ser. No. 60/939,792, which was filed on May 23, 2007. In some examples, the DNA plasmids described herein can be formulated at concentrations greater than or equal to 10 mg/mL. The manufacturing techniques also include or incorporate various devices and protocols that are commonly known to those of ordinary skill in the art, in addition to those described in U.S. Ser. No. 60/939,792, including those described in a licensed patent, U.S. Pat. No. 7,238,522, which issued on Jul. 3, 2007. The above-referenced application and patent, U.S. Ser. No. 60/939,792 and U.S. Pat. No. 7,238,522, respectively, are hereby incorporated in their entirety.

4. Antibody

As described above, the recombinant nucleic acid sequence can encode the antibody, a fragment thereof, a variant thereof, or a combination thereof. The antibody can bind or react with the antigen, which is described in more detail below.

The antibody may comprise a heavy chain and a light chain complementarity determining region ("CDR") set, respectively interposed between a heavy chain and a light chain framework ("FR") set which provide support to the CDRs and define the spatial relationship of the CDRs relative to each other. The CDR set may contain three hypervariable regions of a heavy or light chain V region. Proceeding from the N-terminus of a heavy or light chain, these regions are denoted as "CDR1," "CDR2," and "CDR3," respectively. An antigen-binding site, therefore, may include six CDRs, comprising the CDR set from each of a heavy and a light chain V region.

The proteolytic enzyme papain preferentially cleaves IgG molecules to yield several fragments, two of which (the F(ab) fragments) each comprise a covalent heterodimer that includes an intact antigen-binding site. The enzyme pepsin is able to cleave IgG molecules to provide several fragments, including the F(ab')2 fragment, which comprises both antigen-binding sites. Accordingly, the antibody can be the Fab or F(ab')2. The Fab can include the heavy chain polypeptide and the light chain polypeptide. The heavy chain polypeptide of the Fab can include the VH region and the CH1 region. The light chain of the Fab can include the VL region and CL region.

The antibody can be an immunoglobulin (Ig). The Ig can be, for example, IgA, IgM, IgD, IgE, and IgG. The immunoglobulin can include the heavy chain polypeptide and the light chain polypeptide. The heavy chain polypeptide of the immunoglobulin can include a VH region, a CH1 region, a hinge region, a CH2 region, and a CH3 region. The light chain polypeptide of the immunoglobulin can include a VL region and CL region.

The antibody can be a polyclonal or monoclonal antibody. The antibody can be a chimeric antibody, a single chain antibody, a multivalent antibody, an affinity matured antibody, a human antibody, a humanized antibody, or a fully human antibody. The humanized antibody can be an antibody from a non-human species that binds the desired antigen having one or more complementarily determining regions (CDRs) from the non-human species and framework regions from a human immunoglobulin molecule.

The antibody can be an IgG1 antibody, an IgG2 antibody, an IgG3 antibody, or an IgG4 antibody. The antibody can be a chimera of any of an IgG1 antibody, an IgG2 antibody, an IgG3 antibody, or an IgG4 antibody. In some embodiments, the antibody hinge domain is modified. For example, in one embodiment, the antibody includes the amino acid substitution Ser288Pro.

The antibody can be a bispecific antibody as described below in more detail. The antibody can be a bifunctional antibody as also described below in more detail.

As described above, the antibody can be generated in the subject upon administration of the composition to the subject. The antibody may have a half-life within the subject. In some embodiments, the antibody may be modified to extend or shorten its half-life within the subject. Such modifications are described below in more detail.

The antibody can be defucosylated as described in more detail below.

The antibody may be modified to reduce or prevent antibody-dependent enhancement (ADE) of disease associated with the antigen as described in more detail below.

a. Multivalent Antibody

In one embodiment, the recombinant nucleic acid sequence can encode a higher-order or multivalent antibody.

Exemplary multivalent antibodies include, but are not limited to, triabodies, tetravalent antibodies, peptabodies and hexabodies. A triabody, tetravalent antibody, peptabody and hexabody comprise 3, 4, 5 and 6 variable domains, respectively. The multivalent antibody of the invention may comprise multiple identical variable domains targeting the same antigen or epitope, or alternatively may comprise multiple variable domains targeting two or more different antigens or epitopes.

In one embodiment, the recombinant nucleic acid sequence can encode a heavy chain or a light chain of an antibody comprising one or more mutations in the Fc region to support formation of a multi-valent antibody. For example, in one embodiment, the recombinant nucleic acid sequence can encode a heavy chain of an antibody comprising one or more mutation that enhances Fc:Fc interactions and hexamerization following surface-target binding and increases complement activation. Exemplary IgG Fc mutations that can support formation of multi-valent antibodies include, but are not limited to, mutations of one or more of residues Q311, A339, E430, E345, D356, I253, S254, Y436, Q386, E382, and S440. In one embodiment, a mutation to promote hexamer formation is E345K. In one embodiment, a mutation to promote hexamer formation is E345R. In one embodiment, a mutation to promote hexamer formation is E430G. In one embodiment, a mutation to promote hexamer formation is S440Y. In one embodiment, the hexameric antibody of the invention comprises at least two of E345K, E345R, E430G and S440Y. In one embodiment, the hexameric antibody of the invention comprises E345R, E430G and S440Y.

In one embodiment, the present invention provides a hexabody as described above which comprises 6 identical variable domains of an anti-2C7 antibody comprising a E430G variation. In one embodiment, the hexabody as described above comprises 6 identical 2C7 E430G scFv molecules. In one embodiment, the present invention provides a hexabody as described above which comprises 6 identical variable domains of an anti-2C7 antibody comprising a E345K variation. In one embodiment, the present invention provides a hexabody as described above which comprises 6 identical variable domains of an anti-2C7 RGY antibody comprising E345R, E430G and S440Y variations. In one embodiment, the hexabody as described above comprises 6 identical 2C7 RGY scFv molecules.

In one embodiment, the recombinant nucleic acid sequence can encode a heavy chain, a light chain, or a J chain, or a combination thereof, of an IgM pentameric antibody. Natural immunoglobulin M (IgM) forms a predominantly pentameric complex that also contains a small polypeptide joining (J) chain. The IgM pentamer exhibits a variety of immune response and plays a crucial role in defense against foreign pathogens and self-antigens. Monomeric IgM consists of 14 immunoglobulin domains (two sets of VH-CH1-CH2-CH3-CH4/VL-CL) in four polypeptide chains that form a pentameric component. The pentamer also contains an additional polypeptide, the J chain, which assembles the pentamer by firmly bridging the cysteine residues within the C-terminal region of two neighboring IgM monomers.

b. Bispecific Antibody

The recombinant nucleic acid sequence can encode a bispecific antibody, a fragment thereof, a variant thereof, or a combination thereof. The bispecific antibody can bind or react with two antigens, for example, two of the antigens described below in more detail. The bispecific antibody can be comprised of fragments of two of the antibodies described herein, thereby allowing the bispecific antibody to bind or react with two desired target molecules, which may include the antigen, which is described below in more detail, a ligand, including a ligand for a receptor, a receptor, including a ligand-binding site on the receptor, a ligand-receptor complex, and a marker.

c. Bifunctional Antibody

The recombinant nucleic acid sequence can encode a bifunctional antibody, a fragment thereof, a variant thereof, or a combination thereof. The bifunctional antibody can bind or react with the antigen described below. The bifunctional antibody can also be modified to impart an additional functionality to the antibody beyond recognition of and binding to the antigen. Such a modification can include, but is not limited to, coupling to factor H or a fragment thereof. Factor H is a soluble regulator of complement activation and thus, may contribute to an immune response via complement-mediated lysis (CML).

d. Extension of Antibody Half-Life

As described above, the antibody may be modified to extend or shorten the half-life of the antibody in the subject. The modification may extend or shorten the half-life of the antibody in the serum of the subject.

The modification may be present in a constant region of the antibody. The modification may be one or more amino acid substitutions in a constant region of the antibody that extend the half-life of the antibody as compared to a half-life of an antibody not containing the one or more amino acid substitutions. The modification may be one or more amino acid substitutions in the CH2 domain of the antibody that extend the half-life of the antibody as compared to a half-life of an antibody not containing the one or more amino acid substitutions.

In some embodiments, the one or more amino acid substitutions in the constant region may include replacing a methionine residue in the constant region with a tyrosine residue, a serine residue in the constant region with a threonine residue, a threonine residue in the constant region with a glutamate residue, or any combination thereof, thereby extending the half-life of the antibody.

In other embodiments, the one or more amino acid substitutions in the constant region may include replacing a methionine residue in the CH2 domain with a tyrosine residue, a serine residue in the CH2 domain with a threonine residue, a threonine residue in the CH2 domain with a glutamate residue, or any combination thereof, thereby extending the half-life of the antibody.

e. Defucosylation

The recombinant nucleic acid sequence can encode an antibody that is not fucosylated (i.e., a defucosylated antibody or a non-fucosylated antibody), a fragment thereof, a variant thereof, or a combination thereof. Fucosylation includes the addition of the sugar fucose to a molecule, for example, the attachment of fucose to N-glycans, 0-glycans and glycolipids. Accordingly, in a defucosylated antibody, fucose is not attached to the carbohydrate chains of the constant region. In turn, this lack of fucosylation may improve FcγRIIIa binding and antibody directed cellular cytotoxic (ADCC) activity by the antibody as compared to the fucosylated antibody. Therefore, in some embodiments, the non-fucosylated antibody may exhibit increased ADCC activity as compared to the fucosylated antibody.

The antibody may be modified so as to prevent or inhibit fucosylation of the antibody. In some embodiments, such a modified antibody may exhibit increased ADCC activity as compared to the unmodified antibody. The modification may be in the heavy chain, light chain, or a combination thereof. The modification may be one or more amino acid substitutions in the heavy chain, one or more amino acid substitutions in the light chain, or a combination thereof.

f. Reduced ADE Response

The antibody may be modified to reduce or prevent antibody-dependent enhancement (ADE) of disease associated with the antigen, but still neutralize the antigen.

In some embodiments, the antibody may be modified to include one or more amino acid substitutions that reduce or prevent binding of the antibody to FcγR1a. The one or more amino acid substitutions may be in the constant region of the antibody. The one or more amino acid substitutions may include replacing a leucine residue with an alanine residue in the constant region of the antibody, i.e., also known herein as LA, LA mutation or LA substitution. The one or more amino acid substitutions may include replacing two leucine residues, each with an alanine residue, in the constant region of the antibody and also known herein as LALA, LALA mutation, or LALA substitution. The presence of the LALA substitutions may prevent or block the antibody from binding to FcγR1a, and thus, the modified antibody does not enhance or cause ADE of disease associated with the antigen, but still neutralizes the antigen.

2C7 Antibodies

The anti-2C7 antibody can comprise the light chain amino acid sequence of SEQ ID NO:2, which is encoded by the nucleic acid sequence of SEQ ID NO:1, or a fragment, or variant thereof.

The anti-2C7 antibody can comprise the heavy chain amino acid sequence of SEQ ID NO:4, which is encoded by the nucleic acid sequence of SEQ ID NO:3, or a fragment, or variant thereof. The anti-2C7 antibody can comprise an anti-2C7 E430G antibody comprising the heavy chain amino acid sequence of SEQ ID NO:6, which is encoded by the nucleic acid sequence of SEQ ID NO:5, or a fragment, or variant thereof. The anti-2C7 antibody can comprise an anti-2C7 E345K antibody comprising the heavy chain amino acid sequence of SEQ ID NO:8, which is encoded by the nucleic acid sequence of SEQ ID NO:7, or a fragment, or variant thereof. The anti-2C7 antibody can comprise an anti-2C7 RGY antibody comprising the heavy chain amino acid sequence of SEQ ID NO:10, which is encoded by the nucleic acid sequence of SEQ ID NO:9, or a fragment, or variant thereof. The anti-2C7 antibody can comprise an anti-2C7 D270A/K322A (NOCOMP) antibody comprising the heavy chain amino acid sequence of SEQ ID NO:11, which is encoded by the nucleic acid sequence of SEQ ID NO:12.

In one embodiment, the anti-2C7 synthetic antibody of the invention comprises a light chain amino acid sequence of SEQ ID NO: 2 and a heavy chain amino acid sequence of SEQ ID NO:4, or a fragment, or variant thereof.

In one embodiment, the anti-2C7 E430G synthetic antibody of the invention comprises a light chain amino acid sequence of SEQ ID NO: 2 and a heavy chain amino acid sequence of SEQ ID NO:6, or a fragment, or variant thereof. In one embodiment, anti-2C7 E430G is a hexabody.

In one embodiment, the anti-2C7 E345K synthetic antibody of the invention comprises a light chain amino acid sequence of SEQ ID NO: 2 and a heavy chain amino acid sequence of SEQ ID NO:8, or a fragment, or variant thereof. In one embodiment, anti-2C7 E345K is a hexabody.

In one embodiment, the anti-2C7 RGY synthetic antibody of the invention comprises a light chain amino acid sequence of SEQ ID NO: 2 and a heavy chain amino acid sequence of SEQ ID NO:10, or a fragment, or variant thereof. In one embodiment, anti-2C7 RGY is a hexabody.

In one embodiment, the anti-2C7 NOCOMP synthetic antibody of the invention comprises a light chain amino acid sequence of SEQ ID NO: 2 and a heavy chain amino acid sequence of SEQ ID NO:12, or a fragment, or variant thereof.

In one embodiment, the heavy chain and light chain of the anti-2C7 antibody are encoded on the same nucleic acid molecule, for example on the same plasmid. In one embodiment, the heavy chain and light chain of the anti-2C7 antibody are encoded on separate nucleic acid molecules, for example on separate plasmids, which are then both expressed to allow for generation of the anti-2C7 antibody in vivo.

5. Antigen

The synthetic antibody or multivalent antibody of the invention is directed to an antigen or fragment or variant thereof. The antigen can be a nucleic acid sequence, an amino acid sequence, a polysaccharide or a combination thereof. The nucleic acid sequence can be DNA, RNA, cDNA, a variant thereof, a fragment thereof, or a combination thereof. The amino acid sequence can be a protein, a peptide, a variant thereof, a fragment thereof, or a combination thereof. The polysaccharide can be a nucleic acid encoded polysaccharide.

The antigen can be from a bacterium. The antigen can be associated with bacterial infection. In one embodiment, the antigen can be associated with an *Neisseria gonorrhoeae* infection. In one embodiment, the antigen can be a lipooligosaccharide.

In one embodiment, a synthetic antibody of the invention targets two or more antigens. In one embodiment, at least one antigen of a bispecific antibody is selected from the antigens described herein. In one embodiment, the two or more antigens are selected from the antigens described herein.

Foreign Antigens

In some embodiments, the antigen is foreign. A foreign antigen is any non-self substance (i.e., originates external to the subject) that, when introduced into the body, is capable of stimulating an immune response.

Bacterial Antigens

The foreign antigen can be a bacterial antigen or fragment or variant thereof. The bacterium can be from any one of the following phyla: Acidobacteria, Actinobacteria, Aquificae, Bacteroidetes, Caldiserica, Chlamydiae, Chlorobi, Chloroflexi, Chrysiogenetes, Cyanobacteria, Deferribacteres, Deinococcus-*Thermus*, Dictyoglomi, Elusimicrobia, Fibrobacteres, Firmicutes, Fusobacteria, Gemmatimonadetes, Lentisphaerae, Nitrospira, Planctomycetes, Proteobacteria, Spirochaetes, Synergistetes, Tenericutes, Thermodesulfobacteria, Thermotogae, and Verrucomicrobia.

The bacterium can be a gram positive bacterium or a gram negative bacterium. The bacterium can be an aerobic bacterium or an anerobic bacterium. The bacterium can be an autotrophic bacterium or a heterotrophic bacterium. The bacterium can be a mesophile, a neutrophile, an extremophile, an acidophile, an alkaliphile, a thermophile, a psychrophile, an *halophile*, or an osmophile.

The bacterium can be an anthrax bacterium, an antibiotic resistant bacterium, a disease causing bacterium, a food poisoning bacterium, an infectious bacterium, *Salmonella* bacterium, *Staphylococcus* bacterium, *Streptococcus* bacterium, or tetanus bacterium. The bacterium can be a mycobacteria, *Clostridium tetani, Yersinia pestis, Bacillus anthracis*, methicillin-resistant *Staphylococcus aureus* (MRSA), or *Clostridium difficile*. The bacterium can be *Mycobacterium tuberculosis*.

The foreign antigen can be a bacterial antigen or fragment or variant thereof. The bacterium can be a disease causing bacterium. The bacterium can be a *Neisseria gonorrhoeae* bacterium.

The antigen may be a *Neisseria gonorrhoeae* antigen, or fragment thereof, or variant thereof. The *Neisseria gonorrhoeae* antigen can be from a factor that allows the bacteria to replicate, infect or survive. Such an antigen can be a gonococcal lipooligosaccharide (LOS). In some embodiments, the LOS antigen can be 2C7.

Viral Antigens

The foreign antigen can be a viral antigen, or fragment thereof, or variant thereof. The viral antigen can be from a virus from one of the following families: Adenoviridae, Arenaviridae, Bunyaviridae, Caliciviridae, Coronaviridae, Filoviridae, Hepadnaviridae, Herpesviridae, Orthomyxoviridae, Papovaviridae, Paramyxoviridae, Parvoviridae, Picornaviridae, Poxviridae, Reoviridae, Retroviridae, Rhabdoviridae, or Togaviridae. The viral antigen can be from human immunodeficiency virus (HIV), Chikungunya virus (CHIKV), dengue fever virus, papilloma viruses, for example, human papillomoa virus (HPV), polio virus, hepatitis viruses, for example, hepatitis A virus (HAV), hepatitis B virus (HBV), hepatitis C virus (HCV), hepatitis D virus (HDV), and hepatitis E virus (HEV), smallpox virus (Variola major and minor), vaccinia virus, influenza virus, rhinoviruses, equine encephalitis viruses, rubella virus, yellow fever virus, Norwalk virus, hepatitis A virus, human T-cell leukemia virus (HTLV-I), hairy cell leukemia virus (HTLV-II), California encephalitis virus, Hanta virus (hemorrhagic fever), rabies virus, Ebola fever virus, Marburg virus, measles virus, mumps virus, respiratory syncytial virus (RSV), herpes simplex 1 (oral herpes), herpes simplex 2 (genital herpes), herpes zoster (varicella-zoster, a.k.a., chickenpox), cytomegalovirus (CMV), for example human CMV, Epstein-Barr virus (EBV), flavivirus, foot and mouth disease virus, lassa virus, arenavirus, or cancer causing virus.

Parasitic Antigens

The foreign antigen can be a parasite antigen or fragment or variant thereof. The parasite can be a protozoa, helminth, or ectoparasite. The helminth (i.e., worm) can be a flatworm (e.g., flukes and tapeworms), a thorny-headed worm, or a round worm (e.g., pinworms). The ectoparasite can be lice, fleas, ticks, and mites.

The parasite can be any parasite causing any one of the following diseases: *Acanthamoeba keratitis*, Amoebiasis, Ascariasis, Babesiosis, Balantidiasis, Baylisascariasis, Chagas disease, Clonorchiasis, *Cochliomyia*, Cryptosporidiosis, Diphyllobothriasis, Dracunculiasis, Echinococcosis, Elephantiasis, Enterobiasis, Fascioliasis, Fasciolopsiasis, Filariasis, Giardiasis, Gnathostomiasis, Hymenolepiasis, Isosporiasis, Katayama fever, Leishmaniasis, Lyme disease, Malaria, Metagonimiasis, Myiasis, Onchocerciasis, Pediculosis, Scabies, Schistosomiasis, Sleeping sickness, Strongyloidiasis, Taeniasis, Toxocariasis, Toxoplasmosis, Trichinosis, and Trichuriasis.

The parasite can be *Acanthamoeba, Anisakis, Ascaris lumbricoides*, Botfly, *Balantidium coli*, Bedbug, Cestoda (tapeworm), Chiggers, *Cochliomyia hominivorax, Entamoeba histolytica, Fasciola hepatica, Giardia lamblia*, Hookworm, *Leishmania, Linguatula serrata*, Liver fluke, *Loa loa, Paragonimus*—lung fluke, Pinworm, *Plasmodium falciparum, Schistosoma, Strongyloides stercoralis*, Mite, Tapeworm, *Toxoplasma gondii, Trypanosoma*, Whipworm, or *Wuchereria bancrofti*.

Fungal Antigens

The foreign antigen can be a fungal antigen or fragment or variant thereof. The fungus can be *Aspergillus* species, *Blastomyces dermatitidis, Candida* yeasts (e.g., *Candida albicans*), *Coccidioides, Cryptococcus neoformans, Cryptococcus gattii*, dermatophyte, *Fusarium* species, *Histoplasma capsulatum*, Mucoromycotina, *Pneumocystis jirovecii, Sporothrix schenckii, Exserohilum*, or *Cladosporium*.

Self Antigens

In some embodiments, the antigen is a self antigen. A self antigen may be a constituent of the subject's own body that is capable of stimulating an immune response. In some embodiments, a self antigen does not provoke an immune response unless the subject is in a disease state, e.g., an autoimmune disease.

Self antigens may include, but are not limited to, cytokines, antibodies against viruses such as those listed above including HIV and Dengue, antigens affecting cancer progression or development, and cell surface receptors or transmembrane proteins.

Tumor antigens are proteins that are produced by tumor cells that elicit an immune response, particularly T-cell mediated immune responses. The selection of the antigen binding moiety of the invention will depend on the particular type of cancer to be treated. Tumor antigens are well known in the art and include, for example, a glioma-associated antigen, carcinoembryonic antigen (CEA), (3-human chorionic gonadotropin, alphafetoprotein (AFP), lectin-reactive AFP, thyroglobulin, RAGE-1, MN-CA IX, human telomerase reverse transcriptase, RU1 RU2 (AS), intestinal carboxyl esterase, mut hsp70-2, M-CSF, prostase, prostate-specific antigen (PSA), PAP, NY-ESO-1, LAGE-1a, p53, prostein, PSMA, Her2/neu, survivin and telomerase, prostate-carcinoma tumor antigen-1 (PCTA-1), MAGE, ELF2M, neutrophil elastase, ephrinB2, CD22, insulin growth factor (IGF)-I, IGF-II, IGF-I receptor and mesothelin.

Illustrative examples of a tumor associated surface antigen are CD10, CD19, CD20, CD22, CD33, Fms-like tyrosine kinase 3 (FLT-3, CD135), chondroitin sulfate proteoglycan 4 (CSPG4, melanoma-associated chondroitin sulfate proteoglycan), Epidermal growth factor receptor (EGFR), Her2neu, Her3, IGFR, CD133, IL3R, fibroblast activating protein (FAP), CDCP1, Derlin1, Tenascin, frizzled 1-10, the vascular antigens VEGFR2 (KDR/FLK1), VEGFR3 (FLT4, CD309), PDGFR-α (CD140a), PDGFR-.beta. (CD140b) Endoglin, CLEC14, Tem1-8, and Tie2. Further examples may include A33, CAMPATH-1 (CDw52), Carcinoembryonic antigen (CEA), Carboanhydrase IX (MN/CA IX), CD21, CD25, CD30, CD34, CD37, CD44v6, CD45, CD133, de2-7 EGFR, EGFRvIII, EpCAM, Ep-CAM, Folate-binding protein, G250, Fms-like tyrosine kinase 3 (FLT-3, CD135), c-Kit (CD117), CSF1R (CD115), HLA-DR, IGFR, IL-2 receptor, IL3R, MCSP (Melanoma-associated cell surface chondroitin sulphate proteoglycane), Muc-1, Prostate-specific membrane antigen (PSMA), Prostate stem cell antigen (PSCA), Prostate specific antigen (PSA), and TAG-72. Examples of antigens expressed on the extracellular matrix of tumors are tenascin and the fibroblast activating protein (FAP).

Non-limiting examples of TSA or TAA antigens include the following: Differentiation antigens such as MART-1/MelanA (MART-I), gp100 (Pmel 17), tyrosinase, TRP-1, TRP-2 and tumor-specific multilineage antigens such as MAGE-1, MAGE-3, BAGE, GAGE-1, GAGE-2, p15; overexpressed embryonic antigens such as CEA; overexpressed oncogenes and mutated tumor-suppressor genes such as p53, Ras, HER-2/neu; unique tumor antigens resulting from chromosomal translocations; such as BCR-ABL, E2A-PRL, H4-RET, IGH-IGK, MYL-RAR; and viral antigens, such as the Epstein Barr virus antigens EBVA and the human papillomavirus (HPV) antigens E6 and E7. Other large, protein-based antigens include TSP-180, MAGE-4, MAGE-5, MAGE-6, RAGE, NY-ESO, p185erbB2, p180erbB-3, c-met, nm-23H1, PSA, TAG-72, CA 19-9, CA 72-4, CAM 17.1, NuMa, K-ras, beta-Catenin, CDK4, Mum-1, p 15, p 16, 43-9F, 5T4, 791Tgp72, alpha-fetoprotein, beta-HCG, BCA225, BTAA, CA 125, CA 15-3\CA 27.29\BCAA, CA 195, CA 242, CA-50, CAM43, CD68\P1, CO-029, FGF-5, G250, Ga733\EpCAM, HTgp-175, M344, MA-50, MG7-Ag, MOV18, NB/70K, NY-CO-1, RCAS1, SDCCAG16, TA-90\Mac-2 binding protein\cyclophilin C-associated protein, TAAL6, TAG72, TLP, and TPS.

Aspects of the present invention include compositions for enhancing an immune response against an antigen in a subject in need thereof, comprising a synthetic multivalent antibody capable of generating an immune response in the subject, or a biologically functional fragment or variant thereof.

6. Excipients and Other Components of the Composition

The composition may further comprise a pharmaceutically acceptable excipient. The pharmaceutically acceptable excipient can be functional molecules such as vehicles, carriers, or diluents. The pharmaceutically acceptable excipient can be a transfection facilitating agent, which can include surface active agents, such as immune-stimulating complexes (ISCOMS), Freunds incomplete adjuvant, LPS analog including monophosphoryl lipid A, muramyl peptides, quinone analogs, vesicles such as squalene and squalene, hyaluronic acid, lipids, liposomes, calcium ions, viral proteins, polyanions, polycations, or nanoparticles, or other known transfection facilitating agents.

The transfection facilitating agent is a polyanion, polycation, including poly-L-glutamate (LGS), or lipid. The transfection facilitating agent is poly-L-glutamate, and the poly-L-glutamate may be present in the composition at a concentration less than 6 mg/ml. The transfection facilitating agent may also include surface active agents such as immune-stimulating complexes (ISCOMS), Freunds incomplete adjuvant, LPS analog including monophosphoryl lipid A, muramyl peptides, quinone analogs and vesicles such as squalene and squalene, and hyaluronic acid may also be used administered in conjunction with the composition. The composition may also include a transfection facilitating agent such as lipids, liposomes, including lecithin liposomes or other liposomes known in the art, as a DNA-liposome mixture (see for example W09324640), calcium ions, viral proteins, polyanions, polycations, or nanoparticles, or other known transfection facilitating agents. The transfection facilitating agent is a polyanion, polycation, including poly-L-glutamate (LGS), or lipid. Concentration of the transfection agent in the vaccine is less than 4 mg/ml, less than 2 mg/ml, less than 1 mg/ml, less than 0.750 mg/ml, less than 0.500 mg/ml, less than 0.250 mg/ml, less than 0.100 mg/ml, less than 0.050 mg/ml, or less than 0.010 mg/ml.

The composition may further comprise a genetic facilitator agent as described in U.S. Ser. No. 021,579 filed Apr. 1, 1994, which is fully incorporated by reference.

The composition may comprise DNA at quantities of from about 1 nanogram to 100 milligrams; about 1 microgram to about 10 milligrams; or preferably about 0.1 microgram to about 10 milligrams; or more preferably about 1 milligram to about 2 milligram. In some preferred embodiments, composition according to the present invention comprises about 5 nanogram to about 1000 micrograms of DNA. In some preferred embodiments, composition can contain about 10 nanograms to about 800 micrograms of DNA. In some preferred embodiments, the composition can contain about 0.1 to about 500 micrograms of DNA. In some preferred embodiments, the composition can contain about 1 to about 350 micrograms of DNA. In some preferred embodiments, the composition can contain about 25 to about 250 micrograms, from about 100 to about 200 microgram, from about 1 nanogram to 100 milligrams; from about 1 microgram to about 10 milligrams; from about 0.1 microgram to about 10 milligrams; from about 1 milligram to about 2 milligram, from about 5 nanogram to about 1000 micrograms, from about 10 nanograms to about 800 micrograms, from about 0.1 to about 500 micrograms, from about 1 to about 350 micrograms, from about 25 to about 250 micrograms, from about 100 to about 200 microgram of DNA.

The composition can be formulated according to the mode of administration to be used. An injectable pharmaceutical composition can be sterile, pyrogen free and particulate free. An isotonic formulation or solution can be used. Additives for isotonicity can include sodium chloride, dextrose, mannitol, sorbitol, and lactose. The composition can comprise a vasoconstriction agent. The isotonic solutions can include phosphate buffered saline. The composition can further comprise stabilizers including gelatin and albumin. The stabilizers can allow the formulation to be stable at room or ambient temperature for extended periods of time, including LGS or polycations or polyanions.

7. Method of Generating the Synthetic Antibody

The present invention also relates a method of generating the synthetic antibody or synthetic multivalent antibody. The method can include administering the composition to the subject in need thereof by using the method of delivery described in more detail below. Accordingly, the synthetic antibody or synthetic multivalent antibody is generated in the subject or in vivo upon administration of the composition to the subject.

The method can also include introducing the composition into one or more cells, and therefore, the synthetic antibody can be generated or produced in the one or more cells. The method can further include introducing the composition into one or more tissues, for example, but not limited to, skin and muscle, and therefore, the synthetic antibody can be generated or produced in the one or more tissues.

8. Method of Identifying or Screening for the Antibody

The present invention further relates to a method of identifying or screening for the antibody described above, which is reactive to or binds the antigen described above. The method of identifying or screening for the antibody can use the antigen in methodologies known in those skilled in art to identify or screen for the antibody. Such methodologies can include, but are not limited to, selection of the antibody from a library (e.g., phage display) and immunization of an animal followed by isolation and/or purification of the antibody.

9. Method of Delivery of the Composition

The present invention also relates to a method of delivering the composition to the subject in need thereof. The method of delivery can include, administering the composition to the subject. Administration can include, but is not limited to, DNA injection with and without in vivo electroporation, liposome mediated delivery, and nanoparticle facilitated delivery.

The mammal receiving delivery of the composition may be human, primate, non-human primate, cow, cattle, sheep, goat, antelope, bison, water buffalo, bison, bovids, deer, hedgehogs, elephants, llama, alpaca, mice, rats, and chicken.

The composition may be administered by different routes including orally, parenterally, sublingually, transdermally, rectally, transmucosally, topically, via inhalation, via buccal administration, intrapleurally, intravenous, intraarterial, intraperitoneal, subcutaneous, intramuscular, intranasal intrathecal, and intraarticular or combinations thereof. For veterinary use, the composition may be administered as a suitably acceptable formulation in accordance with normal veterinary practice. The veterinarian can readily determine the dosing regimen and route of administration that is most appropriate for a particular animal. The composition may be administered by traditional syringes, needleless injection devices, "microprojectile bombardment gone guns", or other physical methods such as electroporation ("EP"), "hydrodynamic method", or ultrasound.

Electroporation

Administration of the composition via electroporation may be accomplished using electroporation devices that can be configured to deliver to a desired tissue of a mammal, a pulse of energy effective to cause reversible pores to form in cell membranes, and preferable the pulse of energy is a constant current similar to a preset current input by a user. The electroporation device may comprise an electroporation component and an electrode assembly or handle assembly. The electroporation component may include and incorporate one or more of the various elements of the electroporation devices, including: controller, current waveform generator, impedance tester, waveform logger, input element, status reporting element, communication port, memory component, power source, and power switch. The electroporation may be accomplished using an in vivo electroporation device, for example CELLECTRA EP system (Inovio Pharmaceuticals, Plymouth Meeting, Pa.) or Elgen electroporator (Inovio Pharmaceuticals, Plymouth Meeting, Pa.) to facilitate transfection of cells by the plasmid.

The electroporation component may function as one element of the electroporation devices, and the other elements are separate elements (or components) in communication with the electroporation component. The electroporation component may function as more than one element of the electroporation devices, which may be in communication with still other elements of the electroporation devices separate from the electroporation component. The elements of the electroporation devices existing as parts of one electromechanical or mechanical device may not limited as the elements can function as one device or as separate elements in communication with one another. The electroporation component may be capable of delivering the pulse of energy that produces the constant current in the desired tissue, and includes a feedback mechanism. The electrode assembly may include an electrode array having a plurality of electrodes in a spatial arrangement, wherein the electrode assembly receives the pulse of energy from the electroporation component and delivers same to the desired tissue through the electrodes. At least one of the plurality of electrodes is neutral during delivery of the pulse of energy and measures impedance in the desired tissue and communicates the impedance to the electroporation component. The feedback mechanism may receive the measured impedance and can adjust the pulse of energy delivered by the electroporation component to maintain the constant current.

A plurality of electrodes may deliver the pulse of energy in a decentralized pattern. The plurality of electrodes may deliver the pulse of energy in the decentralized pattern through the control of the electrodes under a programmed sequence, and the programmed sequence is input by a user to the electroporation component. The programmed sequence may comprise a plurality of pulses delivered in sequence, wherein each pulse of the plurality of pulses is delivered by at least two active electrodes with one neutral electrode that measures impedance, and wherein a subsequent pulse of the plurality of pulses is delivered by a different one of at least two active electrodes with one neutral electrode that measures impedance.

The feedback mechanism may be performed by either hardware or software. The feedback mechanism may be performed by an analog closed-loop circuit. The feedback occurs every 50 μs, 20 μs, 10 μs or 1 μs, but is preferably a real-time feedback or instantaneous (i.e., substantially instantaneous as determined by available techniques for determining response time). The neutral electrode may measure the impedance in the desired tissue and communicates the impedance to the feedback mechanism, and the feedback mechanism responds to the impedance and adjusts the pulse of energy to maintain the constant current at a value similar to the preset current. The feedback mechanism may maintain the constant current continuously and instantaneously during the delivery of the pulse of energy.

Examples of electroporation devices and electroporation methods that may facilitate delivery of the composition of the present invention, include those described in U.S. Pat. No. 7,245,963 by Draghia-Akli, et al., U.S. Patent Pub. 2005/0052630 submitted by Smith, et al., the contents of which are hereby incorporated by reference in their entirety.

Other electroporation devices and electroporation methods that may be used for facilitating delivery of the composition include those provided in co-pending and co-owned U.S. patent application Ser. No. 11/874,072, filed Oct. 17, 2007, which claims the benefit under 35 USC 119(e) to U.S. Provisional Application Ser. No. 60/852,149, filed Oct. 17, 2006, and 60/978,982, filed Oct. 10, 2007, all of which are hereby incorporated in their entirety.

U.S. Pat. No. 7,245,963 by Draghia-Akli, et al. describes modular electrode systems and their use for facilitating the introduction of a biomolecule into cells of a selected tissue in a body or plant. The modular electrode systems may comprise a plurality of needle electrodes; a hypodermic needle; an electrical connector that provides a conductive link from a programmable constant-current pulse controller to the plurality of needle electrodes; and a power source. An operator can grasp the plurality of needle electrodes that are mounted on a support structure and firmly insert them into the selected tissue in a body or plant. The biomolecules are then delivered via the hypodermic needle into the selected tissue. The programmable constant-current pulse controller is activated and constant-current electrical pulse is applied to the plurality of needle electrodes. The applied constant-current electrical pulse facilitates the introduction of the biomolecule into the cell between the plurality of electrodes. The entire content of U.S. Pat. No. 7,245,963 is hereby incorporated by reference.

U.S. Patent Pub. 2005/0052630 submitted by Smith, et al. describes an electroporation device which may be used to effectively facilitate the introduction of a biomolecule into cells of a selected tissue in a body or plant. The electroporation device comprises an electro-kinetic device ("EKD device") whose operation is specified by software or firmware. The EKD device produces a series of programmable constant-current pulse patterns between electrodes in an array based on user control and input of the pulse parameters, and allows the storage and acquisition of current waveform data. The electroporation device also comprises a replaceable electrode disk having an array of needle electrodes, a central injection channel for an injection needle, and a removable guide disk. The entire content of U.S. Patent Pub. 2005/0052630 is hereby incorporated by reference.

The electrode arrays and methods described in U.S. Pat. No. 7,245,963 and U.S. Patent Pub. 2005/0052630 may be adapted for deep penetration into not only tissues such as muscle, but also other tissues or organs. Because of the configuration of the electrode array, the injection needle (to deliver the biomolecule of choice) is also inserted completely into the target organ, and the injection is administered perpendicular to the target issue, in the area that is pre-delineated by the electrodes The electrodes described in U.S. Pat. No. 7,245,963 and U.S. Patent Pub. 2005/005263 are preferably 20 mm long and 21 gauge.

Additionally, contemplated in some embodiments that incorporate electroporation devices and uses thereof, there are electroporation devices that are those described in the following patents: U.S. Pat. No. 5,273,525 issued Dec. 28, 1993, U.S. Pat. No. 6,110,161 issued Aug. 29, 2000, U.S. Pat. No. 6,261,281 issued Jul. 17, 2001, and U.S. Pat. No. 6,958,060 issued Oct. 25, 2005, and U.S. Pat. No. 6,939,862 issued Sep. 6, 2005. Furthermore, patents covering subject matter provided in U.S. Pat. No. 6,697,669 issued Feb. 24, 2004, which concerns delivery of DNA using any of a variety of devices, and U.S. Pat. No. 7,328,064 issued Feb.

5, 2008, drawn to method of injecting DNA are contemplated herein. The above-patents are incorporated by reference in their entirety.

10. Method of Treatment

Also provided herein is a method of treating, protecting against, and/or preventing disease in a subject in need thereof by generating the synthetic antibody or synthetic multivalent antibody in the subject. The method can include administering the composition to the subject. Administration of the composition to the subject can be done using the method of delivery described above.

In certain embodiments, the invention provides a method of treating protecting against, and/or preventing a disease or disorder associated with a target of the synthetic antibody or synthetic multivalent antibody. In various embodiments, the disease or disorder is a bacterial infection, a viral infection, a fungal infection, a disease or disorder associated with a parasite, or a disease or disorder associated with a self antigen, including, but not limited to, cancer.

In certain embodiments, the invention provides a method of treating protecting against, and/or preventing a *Neisseria gonorrhoeae* infection. In one embodiment, the method improves clearance of a *Neisseria gonorrhoeae* infection. In one embodiment, the method protects the subject from a *Neisseria gonorrhoeae* infection Upon generation of the synthetic antibody in the subject, the synthetic antibody can bind to or react with the antigen. Such binding can neutralize the antigen, block recognition of the antigen by another molecule, for example, a protein or nucleic acid, and elicit or induce an immune response to the antigen, thereby treating, protecting against, and/or preventing the disease associated with the antigen in the subject.

The composition dose can be between 1 μg to 10 mg active component/kg body weight/time, and can be 20 μg to 10 mg component/kg body weight/time. The composition can be administered every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days. The number of composition doses for effective treatment can be 1, 2, 3, 4, 5, 6, 7, 8, 9, or 10.

11. Use in Combination with Antibiotics

The present invention also provides a method of treating, protecting against, and/or preventing disease in a subject in need thereof by administering a combination of the synthetic antibody and a therapeutic antibiotic agent.

The synthetic antibody and an antibiotic agent may be administered using any suitable method such that a combination of the synthetic antibody and antibiotic agent are both present in the subject. In one embodiment, the method may comprise administration of a first composition comprising a synthetic antibody of the invention by any of the methods described in detail above and administration of a second composition comprising an antibiotic agent less than 1, less than 2, less than 3, less than 4, less than 5, less than 6, less than 7, less than 8, less than 9 or less than 10 days following administration of the synthetic antibody. In one embodiment, the method may comprise administration of a first composition comprising a synthetic antibody of the invention by any of the methods described in detail above and administration of a second composition comprising an antibiotic agent more than 1, more than 2, more than 3, more than 4, more than 5, more than 6, more than 7, more than 8, more than 9 or more than 10 days following administration of the synthetic antibody. In one embodiment, the method may comprise administration of a first composition comprising an antibiotic agent and administration of a second composition comprising a synthetic antibody of the invention by any of the methods described in detail above less than 1, less than 2, less than 3, less than 4, less than 5, less than 6, less than 7, less than 8, less than 9 or less than 10 days following administration of the antibiotic agent. In one embodiment, the method may comprise administration of a first composition comprising an antibiotic agent and administration of a second composition comprising a synthetic antibody of the invention by any of the methods described in detail above more than 1, more than 2, more than 3, more than 4, more than 5, more than 6, more than 7, more than 8, more than 9 or more than 10 days following administration of the antibiotic agent. In one embodiment, the method may comprise administration of a first composition comprising a synthetic antibody of the invention by any of the methods described in detail above and a second composition comprising an antibiotic agent concurrently. In one embodiment, the method may comprise administration of a first composition comprising a synthetic antibody of the invention by any of the methods described in detail above and a second composition comprising an antibiotic agent concurrently. In one embodiment, the method may comprise administration of a single composition comprising a synthetic antibody of the invention and an antibiotic agent.

Non-limiting examples of antibiotics that can be used in combination with the synthetic antibody of the invention include aminoglycosides (e.g., gentamicin, amikacin, tobramycin), quinolones (e.g., ciprofloxacin, levofloxacin), cephalosporins (e.g., ceftazidime, cefepime, cefoperazone, cefpirome, ceftobiprole), antipseudomonal penicillins: carboxypenicillins (e.g., carbenicillin and ticarcillin) and ureidopenicillins (e.g., mezlocillin, azlocillin, and piperacillin), carbapenems (e.g., meropenem, imipenem, doripenem), polymyxins (e.g., polymyxin B and colistin) and monobactams (e.g., aztreonam).

12. Cancer Therapy

In one embodiment, the invention provides methods of treating or preventing cancer, or of treating and preventing growth or metastasis of tumors. Related aspects of the invention provide methods of preventing, aiding in the prevention, and/or reducing metastasis of hyperplastic or tumor cells in an individual.

One aspect of the invention provides a method of inhibiting metastasis in an individual in need thereof, the method comprising administering to the individual an effective amount of a nucleic acid molecule encoding a multivalent antibody of the invention, wherein the multivalent antibody is specific for the cancer to be treated. The invention further provides a method of inhibiting metastasis in an individual in need thereof, the method comprising administering to the individual an effective metastasis-inhibiting amount of a nucleic acid molecule encoding a multivalent antibody of the invention, wherein the multivalent antibody is specific for the cancer to be treated.

In some embodiments of treating or preventing cancer, or of treating and preventing metastasis of tumors in an individual in need thereof, a second agent is administered to the individual, such as an antineoplastic agent. In some embodiments, the second agent comprises a second metastasis-inhibiting agent, such as a plasminogen antagonist, or an adenosine deaminase antagonist. In other embodiments, the second agent is an angiogenesis inhibiting agent.

The compositions of the invention can be used to prevent, abate, minimize, control, and/or lessen cancer in humans and animals. The compositions of the invention can also be used to slow the rate of primary tumor growth. The compositions of the invention when administered to a subject in need of treatment can be used to stop the spread of cancer cells. As such, an effective amount of a nucleic acid molecule encoding a multivalent antibody of the invention, wherein the multivalent antibody is specific for the cancer to be treated can be administered as part of a combination therapy with one or more drugs or other pharmaceutical agents. When used as part of the combination therapy, the decrease in metastasis and reduction in primary tumor growth afforded by the compositions of the invention allows for a more effective and efficient use of any pharmaceutical or drug therapy being used to treat the patient. In addition, control of metastasis by the compositions of the invention affords the subject a greater ability to concentrate the disease in one location.

In one embodiment, the invention provides methods for preventing metastasis of malignant tumors or other cancerous cells as well as to reduce the rate of tumor growth. The methods comprise administering an effective amount of a nucleic acid molecule encoding a multivalent antibody of the invention, wherein the multivalent antibody is specific for the cancer to be treated, to a subject diagnosed with a malignant tumor or cancerous cells or to a subject having a tumor or cancerous cells.

The following are non-limiting examples of cancers that can be treated by the methods and compositions of the invention: Acute Lymphoblastic; Acute Myeloid Leukemia; Adrenocortical Carcinoma; Adrenocortical Carcinoma, Childhood; Appendix Cancer; Basal Cell Carcinoma; Bile Duct Cancer, Extrahepatic; Bladder Cancer; Bone Cancer; Osteosarcoma and Malignant Fibrous Histiocytoma; Brain Stem Glioma, Childhood; Brain Tumor, Adult; Brain Tumor, Brain Stem Glioma, Childhood; Brain Tumor, Central Nervous System Atypical Teratoid/Rhabdoid Tumor, Childhood; Central Nervous System Embryonal Tumors; Cerebellar Astrocytoma; Cerebral Astrocytotna/Malignant Glioma; Craniopharyngioma; Ependymoblastoma; Ependymoma; Medulloblastoma; Medulloepithelioma; Pineal Parenchymal Tumors of intermediate Differentiation; Supratentorial Primitive Neuroectodermal Tumors and Pineoblastoma; Visual Pathway and Hypothalamic Glioma; Brain and Spinal Cord Tumors; Breast Cancer; Bronchial Tumors; Burkitt Lymphoma; Carcinoid Tumor; Carcinoid Tumor, Gastrointestinal; Central Nervous System Atypical Teratoid/Rhabdoid Tumor; Central Nervous System Embryonal Tumors; Central Nervous System Lymphoma; Cerebellar Astrocytoma Cerebral Astrocytoma/Malignant Glioma, Childhood; Cervical Cancer; Chordoma, Childhood; Chronic Lymphocytic Leukemia; Chronic Myelogenous Leukemia; Chronic Myeloproliferative Disorders; Colon Cancer; Colorectal Cancer; Craniopharyngioma; Cutaneous T-Cell Lymphoma; Esophageal Cancer; Ewing Family of Tumors; Extragonadal Germ Cell Tumor; Extrahepatic Bile Duct Cancer; Eye Cancer, intraocular Melanoma; Eye Cancer, Retinoblastoma; Gallbladder Cancer; Gastric (Stomach) Cancer; Gastrointestinal Carcinoid Tumor; Gastrointestinal Stromal Tumor (GIST); Germ Cell Tumor, Extracranial; Germ Cell Tumor, Extragonadal; Germ Cell Tumor, Ovarian; Gestational Trophoblastic Tumor; Glioma; Glioma, Childhood Brain Stem; Glioma, Childhood Cerebral Astrocytoma; Glioma, Childhood Visual Pathway and Hypothalamic; Hairy Cell Leukemia; Head and Neck Cancer; Hepatocellular (Liver) Cancer; Histiocytosis, Langerhans Cell; Hodgkin Lymphoma; Hypopharyngeal Cancer; Hypothalamic and Visual Pathway Glioma; intraocular Melanoma; Islet Cell Tumors; Kidney (Renal Cell) Cancer; Langerhans Cell Histiocytosis; Laryngeal Cancer; Leukemia, Acute Lymphoblastic; Leukemia, Acute Myeloid; Leukemia, Chronic Lymphocytic; Leukemia, Chronic Myelogenous; Leukemia, Hairy Cell; Lip and Oral Cavity Cancer; Liver Cancer; Lung Cancer, Non-Small Cell; Lung Cancer, Small Cell; Lymphoma, AIDS-Related; Lymphoma, Burkitt; Lymphoma, Cutaneous T-Cell; Lymphoma, Hodgkin; Lymphoma, Non-Hodgkin; Lymphoma, Primary Central Nervous System; Macroglobulinemia, Waldenstrom; Malignant Fibrous Histiocvtoma of Bone and Osteosarcoma; Medulloblastoma; Melanoma; Melanoma, intraocular (Eye); Merkel Cell Carcinoma; Mesothelioma; Metastatic Squamous Neck Cancer with Occult Primary; Mouth Cancer; Multiple Endocrine Neoplasia Syndrome, (Childhood); Multiple Myeloma/Plasma Cell Neoplasm; Mycosis; Fungoides; Myelodysplastic Syndromes; Myelodysplastic/Myeloproliferative Diseases; Myelogenous Leukemia, Chronic; Myeloid Leukemia, Adult Acute; Myeloid Leukemia, Childhood Acute; Myeloma, Multiple; Myeloproliferative Disorders, Chronic; Nasal Cavity and Paranasal Sinus Cancer; Nasopharyngeal Cancer; Neuroblastoma; Non-Small Cell Lung Cancer; Oral Cancer; Oral Cavity Cancer; Oropharyngeal Cancer; Osteosarcoma and Malignant Fibrous Histiocytoma of Bone; Ovarian Cancer; Ovarian Epithelial Cancer; Ovarian Germ Cell Tumor; Ovarian Low Malignant Potential Tumor; Pancreatic Cancer; Pancreatic Cancer, Islet Cell Tumors; Papillomatosis; Parathyroid Cancer; Penile Cancer; Pharyngeal Cancer; Pheochromocytoma; Pineal Parenchymal Tumors of Intermediate Differentiation; Pineoblastoma and Supratentorial Primitive Neuroectodermal Tumors; Pituitary Tumor; Plasma Celt Neoplasm/Multiple Myeloma; Pleuropulmonary Blastoma; Primary Central Nervous System Lymphoma; Prostate Cancer; Rectal Cancer; Renal Cell (Kidney) Cancer; Renal Pelvis and Ureter, Transitional Cell Cancer; Respiratory Tract Carcinoma Involving the NUT Gene on Chromosome 15; Retinoblastoma; Rhabdomyosarcoma; Salivary Gland Cancer; Sarcoma, Ewing Family of Tumors; Sarcoma, Kaposi; Sarcoma, Soft Tissue; Sarcoma, Uterine; Sezary Syndrome; Skin Cancer (Nonmelanoma); Skin Cancer (Melanoma); Skin Carcinoma, Merkel Cell; Small Cell Lung Cancer; Small Intestine Cancer; Soft Tissue Sarcoma; Squamous Cell Carcinoma, Squamous Neck Cancer with Occult Primary, Metastatic; Stomach (Gastric) Cancer; Supratentorial Primitive Neuroectodermal Tumors; T-Cell Lymphoma, Cutaneous; Testicular Cancer; Throat Cancer; Thymoma and Thymic Carcinoma; Thyroid Cancer; Transitional Cell Cancer of the Renal Pelvis and Ureter; Trophoblastic Tumor, Gestational; Urethral Cancer; Uterine Cancer, Endometrial; Uterine Sarcoma; Vaginal Cancer; Vulvar Cancer; Waldenstrom Macroglobulinemia; and Wilms Tumor.

In one embodiment, the invention provides a method to treat cancer metastasis comprising treating the subject prior to, concurrently with, or subsequently to the treatment with a composition of the invention, with a complementary therapy for the cancer, such as surgery, chemotherapy, chemotherapeutic agent, radiation therapy, or hormonal therapy or a combination thereof.

Chemotherapeutic agents include cytotoxic agents (e.g., 5-fluorouracil, cisplatin, carboplatin, methotrexate, daunorubicin, doxorubicin, vincristine, vinblastine, oxorubicin, carmustine (BCNU), lomustine (CCNU), cytarabine USP, cyclophosphamide, estramucine phosphate sodium, altretamine, hydroxyurea, ifosfamide, procarbazine, mitomycin, busulfan, cyclophosphamide, mitoxantrone, carboplatin, cisplatin, interferon alfa-2a recombinant, paclitaxel, teniposide, and streptozoci), cytotoxic alkylating agents (e.g., busulfan, chlorambucil, cyclophosphamide, melphalan, or ethylesulfonic acid), alkylating agents (e.g., asaley, AZQ, BCNU, busulfan, bisulphan, carboxyphthalatoplatinum, CBDCA, CCNU, CHIP, chlorambucil, chlorozotocin, cisplatinum, clomesone, cyanomorpholinodoxorubicin, cyclodisone, cyclophosphamide, dianhydrogalactitol, fluorodopan, hepsulfam, hycanthone, iphosphamide, melphalan, methyl CCNU, mitomycin C, mitozolamide, nitrogen mustard, PCNU, piperazine, piperazinedione, pipobroman, porfiromycin, spirohydantoin mustard, streptozotocin, teroxirone, tetraplatin, thiotepa, triethylenemelamine, uracil nitrogen mustard, and Yoshi-864), antimitotic agents (e.g., allocolchicine, Halichondrin M, colchicine, colchicine derivatives, dolastatin 10, maytansine, rhizoxin, paclitaxel derivatives, paclitaxel, thiocolchicine, trityl cysteine, vinblastine sulfate, and vincristine sulfate), plant alkaloids (e.g., actinomycin D, bleomycin, L-asparaginase, idarubicin, vinblastine sulfate, vincristine sulfate, mitramycin, mitomycin, daunorubicin, VP-16-213, VM-26, navelbine and taxotere), biologicals (e.g., alpha interferon, BCG, G-CSF, GM-CSF, and interleukin-2), topoisomerase I inhibitors (e.g., camptothecin, camptothecin derivatives, and morpholinodoxorubicin), topoisomerase II inhibitors (e.g., mitoxantron, amonafide, m-AMSA, anthrapyrazole derivatives, pyrazoloacridine, bisantrene HCL, daunorubicin, deoxydoxorubicin, menogaril, N,N-dibenzyl daunomycin, oxanthrazole, rubidazone, VM-26 and VP-16), and synthetics (e.g., hydroxyurea, procarbazine, o,p'-DDD, dacarbazine, CCNU, BCNU, cis-diamminedichloroplatimun, mitoxantrone, CBDCA, levamisole, hexamethylmelamine, all-trans retinoic acid, gliadel and porfimer sodium).

Antiproliferative agents are compounds that decrease the proliferation of cells. Antiproliferative agents include alkylating agents, antimetabolites, enzymes, biological response modifiers, miscellaneous agents, hormones and antagonists, androgen inhibitors (e.g., flutamide and leuprolide acetate), antiestrogens (e.g., tamoxifen citrate and analogs thereof, toremifene, droloxifene and roloxifene), Additional examples of specific antiproliferative agents include, but are not limited to levamisole, gallium nitrate, granisetron, sargramostim strontium-89 chloride, filgrastim, pilocarpine, dexrazoxane, and ondansetron.

The compounds of the invention can be administered alone or in combination with other anti-tumor agents, including cytotoxic/antineoplastic agents and anti-angiogenic agents. Cytotoxic/anti-neoplastic agents are defined as agents which attack and kill cancer cells. Some cytotoxic/anti-neoplastic agents are alkylating agents, which alkylate the genetic material in tumor cells, e.g., cis-platin, cyclophosphamide, nitrogen mustard, trimethylene thiophosphoramide, carmustine, busulfan, chlorambucil, belustine, uracil mustard, chlomaphazin, and dacabazine. Other cytotoxic/anti-neoplastic agents are antimetabolites for tumor cells, e.g., cytosine arabinoside, fluorouracil, methotrexate, mercaptopuirine, azathioprime, and procarbazine. Other cytotoxic/anti-neoplastic agents are antibiotics, e.g., doxorubicin, bleomycin, dactinomycin, daunorubicin, mithramycin, mitomycin, mytomycin C, and daunomycin. There are numerous liposomal formulations commercially available for these compounds. Still other cytotoxic/anti-neoplastic agents are mitotic inhibitors (vinca alkaloids). These include vincristine, vinblastine and etoposide. Miscellaneous cytotoxic/anti-neoplastic agents include taxol and its derivatives, L-asparaginase, anti-tumor antibodies, dacarbazine, azacytidine, amsacrine, melphalan, VM-26, ifosfamide, mitoxantrone, and vindesine.

Anti-angiogenic agents are well known to those of skill in the art. Suitable anti-angiogenic agents for use in the methods and compositions of the invention include anti-VEGF antibodies, including humanized and chimeric antibodies, anti-VEGF aptamers and antisense oligonucleotides. Other known inhibitors of angiogenesis include angiostatin, endostatin, interferons, interleukin 1 (including alpha and beta) interleukin 12, retinoic acid, and tissue inhibitors of metalloproteinase-1 and -2. (TIMP-1 and -2). Small molecules, including topoisomerases such as razoxane, a topoisomerase II inhibitor with anti-angiogenic activity, can also be used.

Other anti-cancer agents that can be used in combination with the compositions of the invention include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-nl; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride. Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer. In one embodiment, the anti-cancer drug is 5-fluorouracil, taxol, or leucovorin.

13. Generation of Synthetic Antibodies in Vitro and Ex Vivo

In one embodiment, the synthetic multivalent antibody of the invention is generated in vitro or ex vivo. For example, in one embodiment, a nucleic acid encoding a synthetic multivalent antibody can be introduced and expressed in an in vitro or ex vivo cell. Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2012, Molecular Cloning: A Laboratory Manual, Cold Spring Harbor Laboratory, New York). A preferred method for the introduction of a polynucleotide into a host cell is calcium phosphate transfection.

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

14. Examples

The present invention is further illustrated in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

Figure 2:
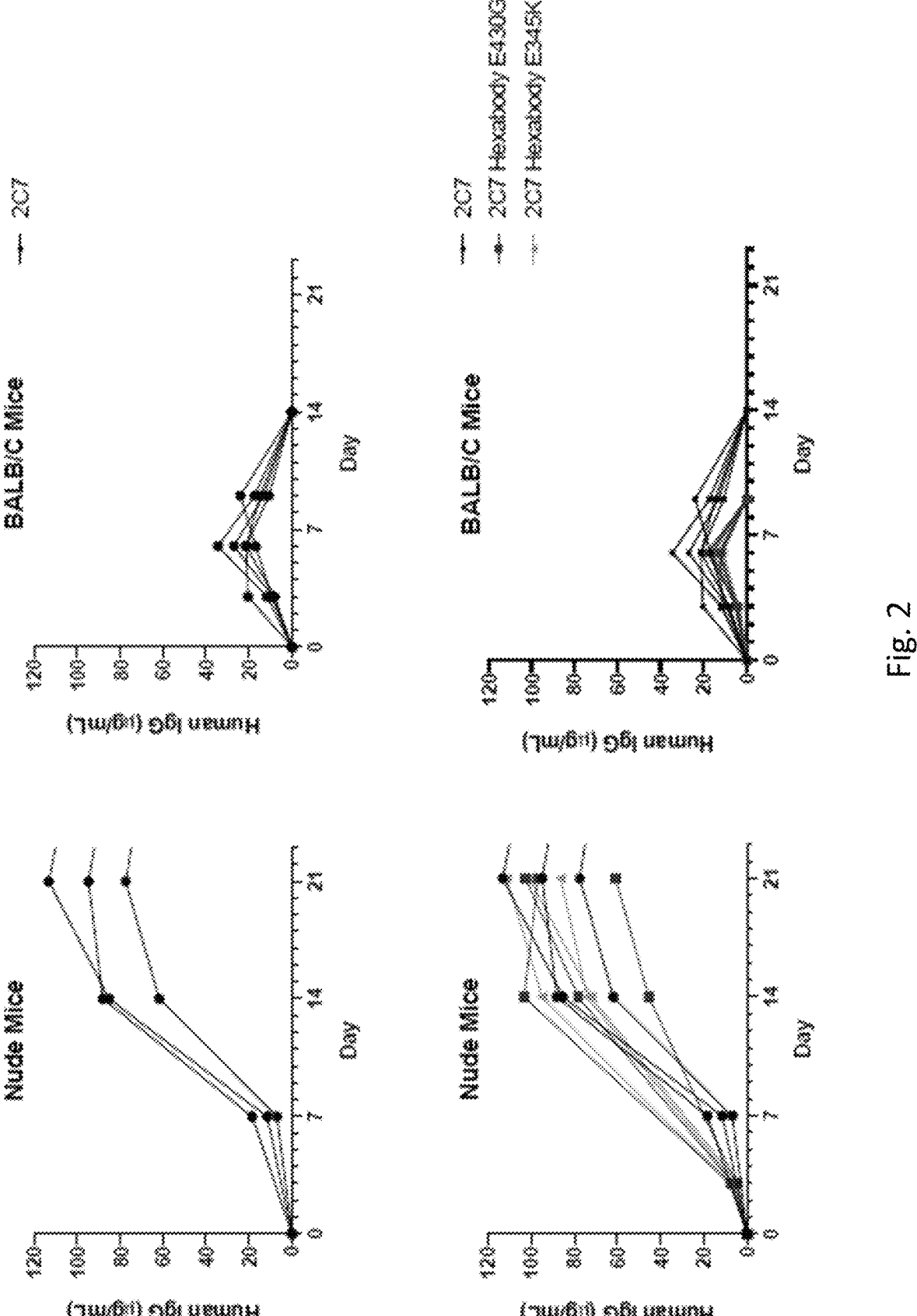
FIG. 2 depicts exemplary experimental results demonstrating the in vivo expression of the 2C7 DMAb and the E345K and E430G hexabody variants.
Figure 3:
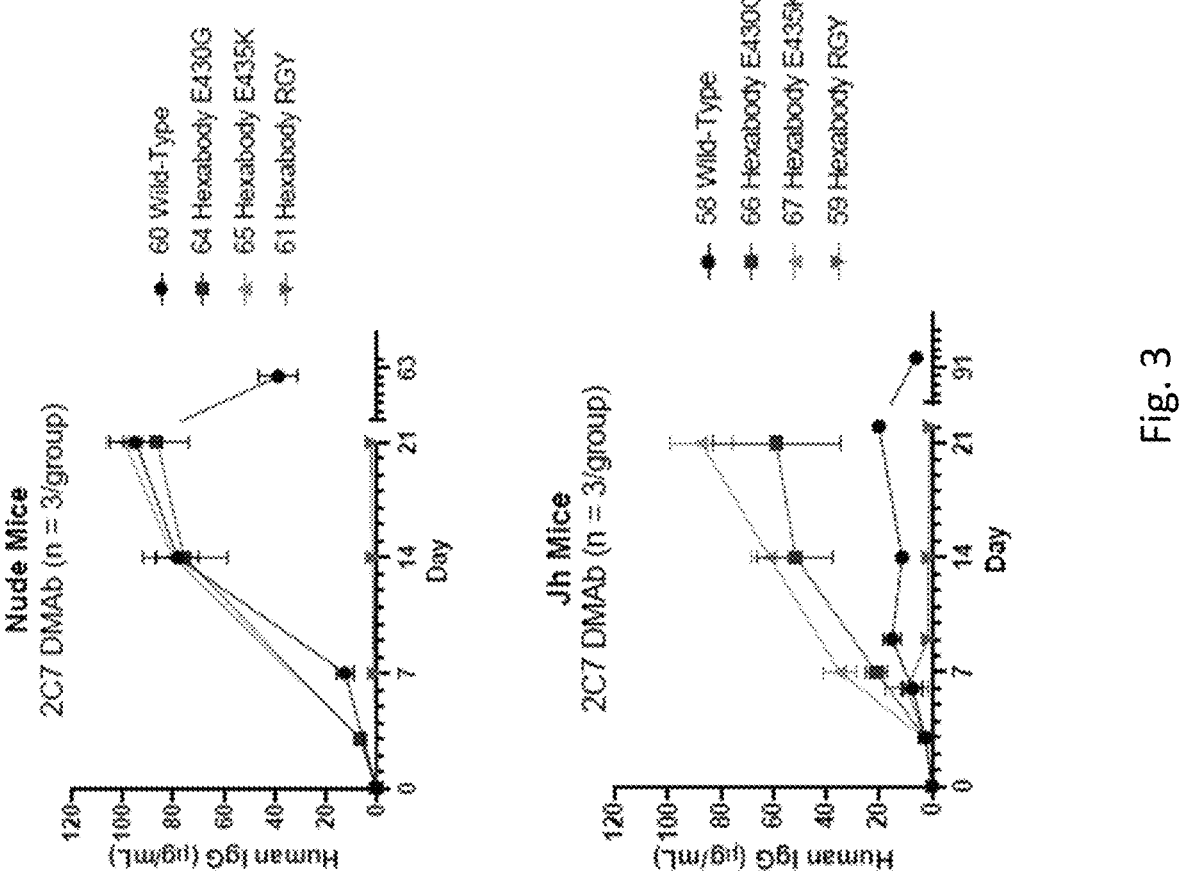
FIG. 3 depicts exemplary experimental results demonstrating the in vivo expression of 2C7 variants in Jh(D) mice is robust, demonstrating similar kinetics as observed in Nude mice.
Figure 5:
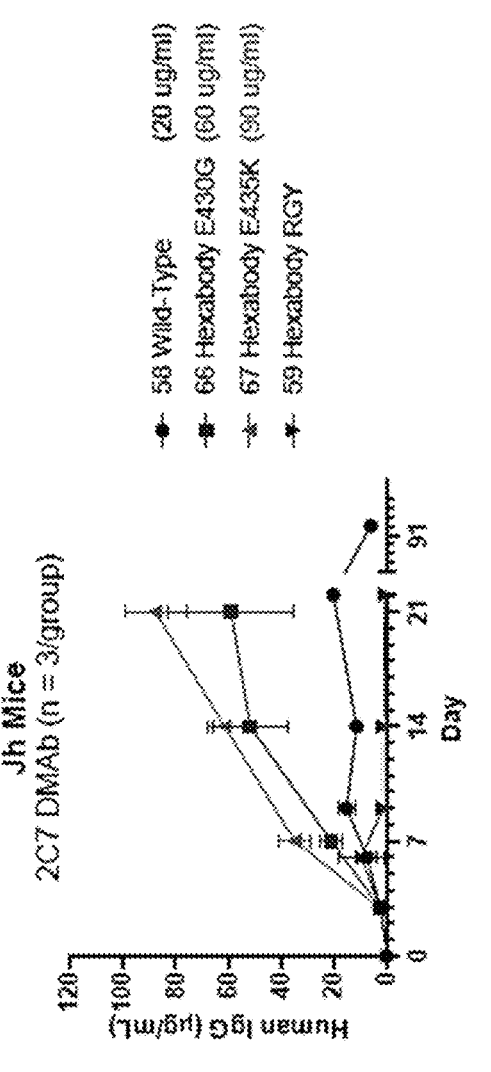
FIG. 5 depicts serum DMAb concentrations.
Figure 5:
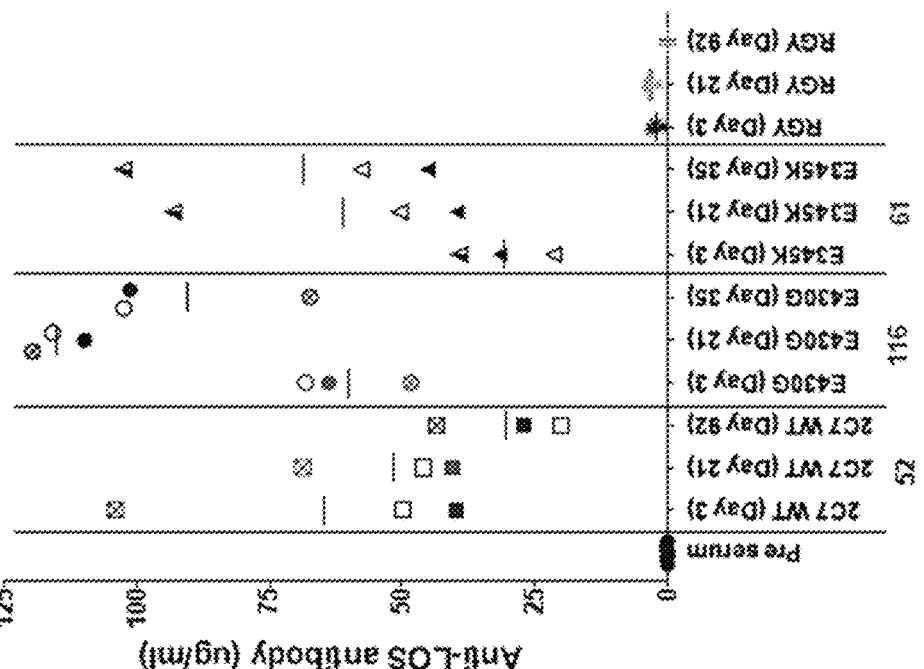
Figure 6:
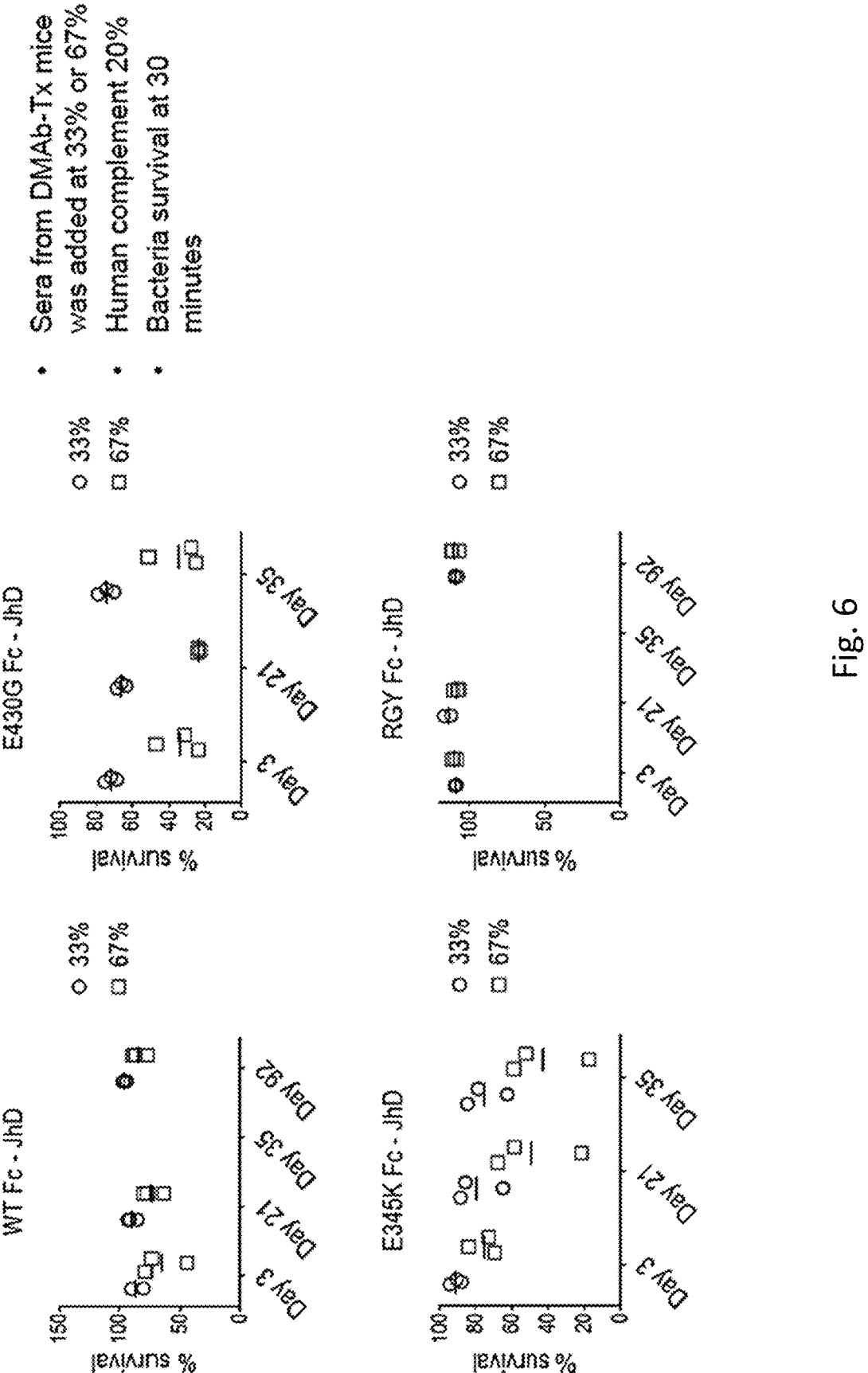
FIG. 6 depicts bactericidal activity in sera of DMAb treated Jh mice persists up to 92 day post-DMAb delivery.
Figure 7:
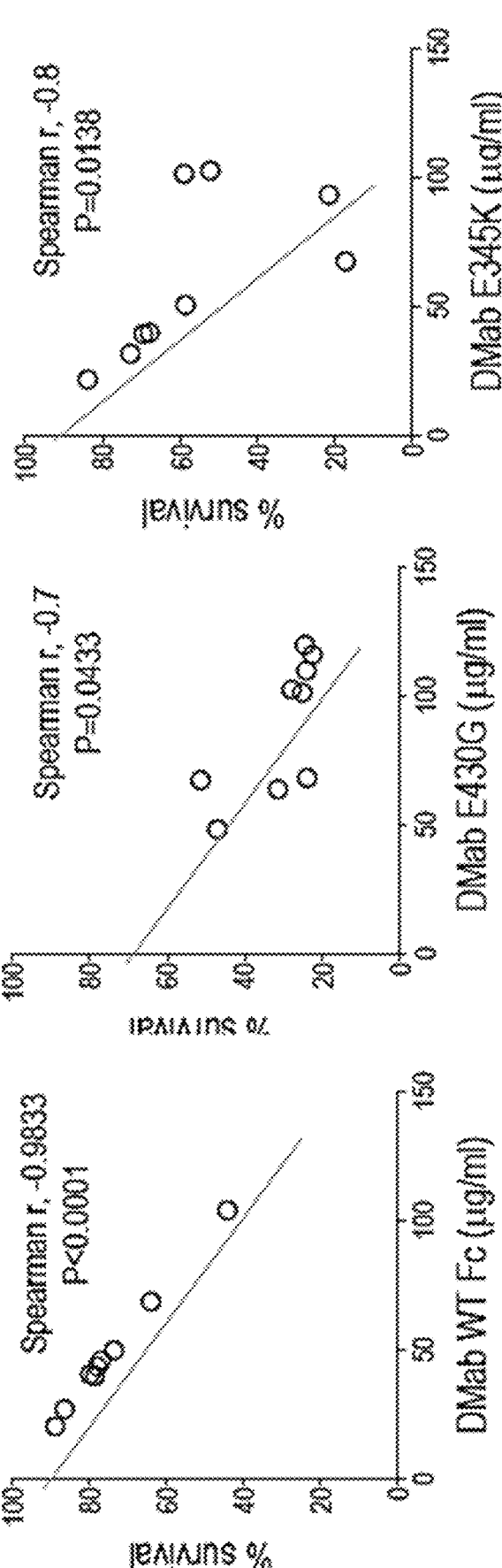
FIG. 7 depicts experimental results demonstrating that the bactericidal potency correlated with serum concentration.
Figure 8:
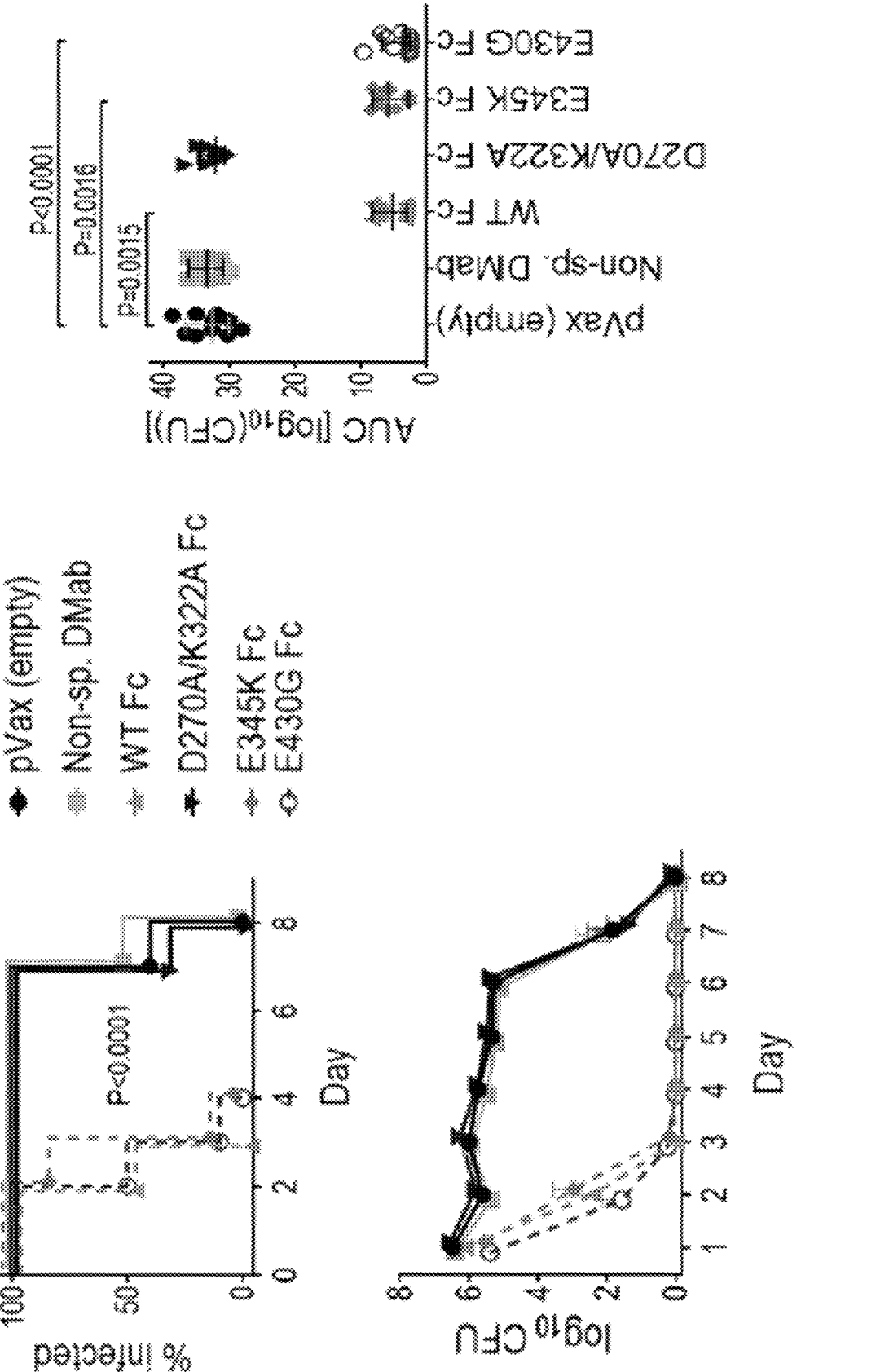
FIG. 8 depicts experimental results demonstrating the efficacy of 2C7-based DMAb variants against *N. gonorrhoeae* (FA1090).
Figure 9:
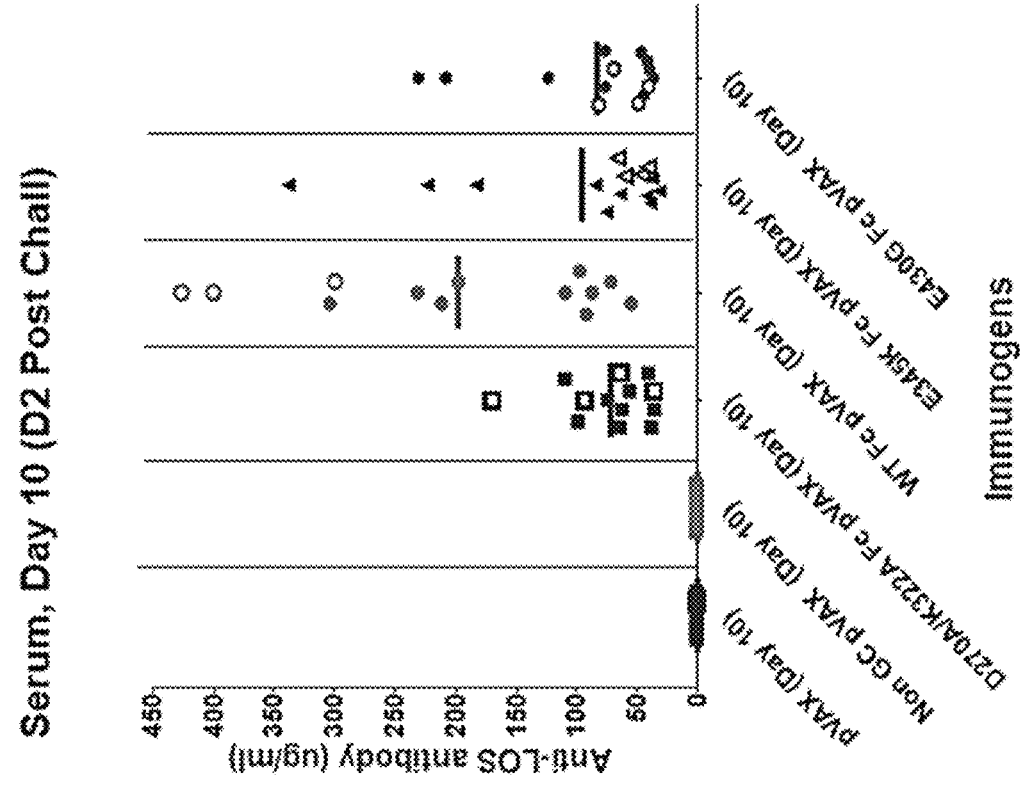
FIG. 9 depicts experimental results demonstrating the DMAb expression in challenged JhD mice.
Figure 9:
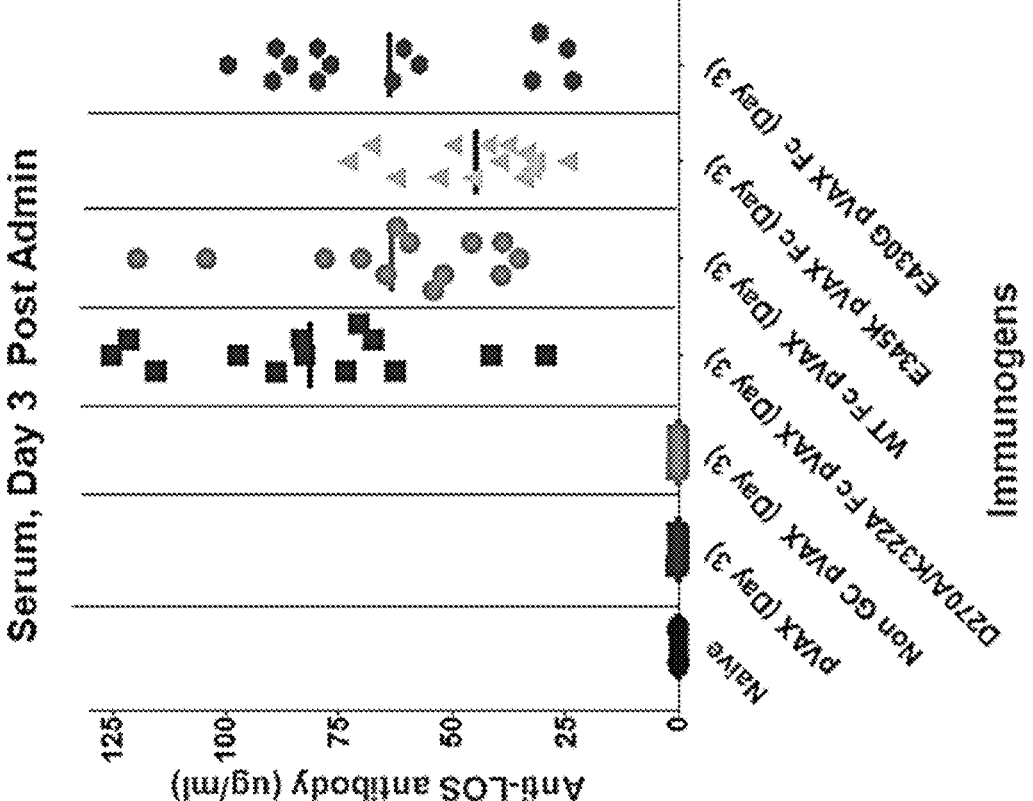
Figure 10:
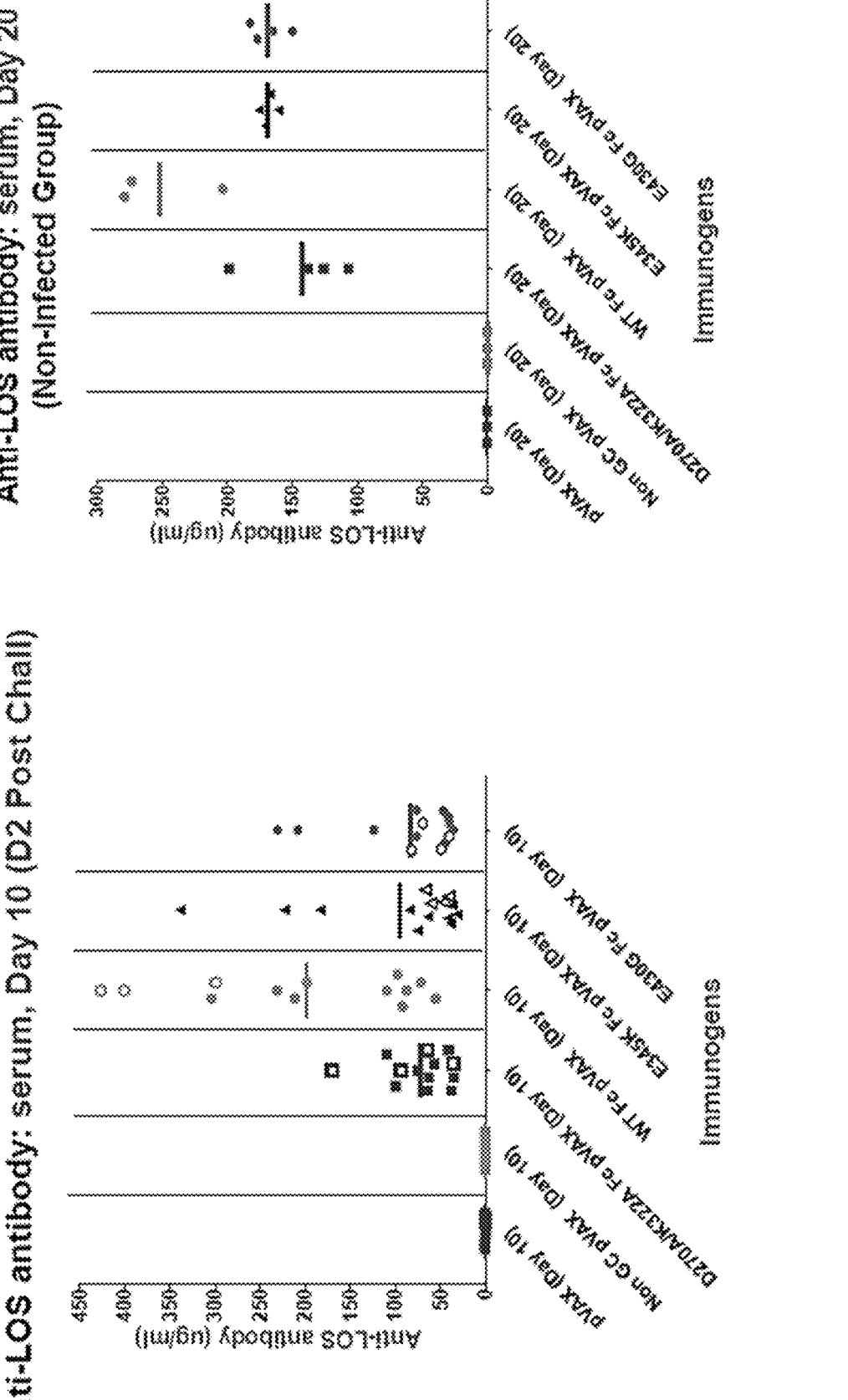
FIG. 10 depicts experimental results demonstrating the DMAb expression in sera at day 10 and 20 of challenged JhD mice.
Figure 11:
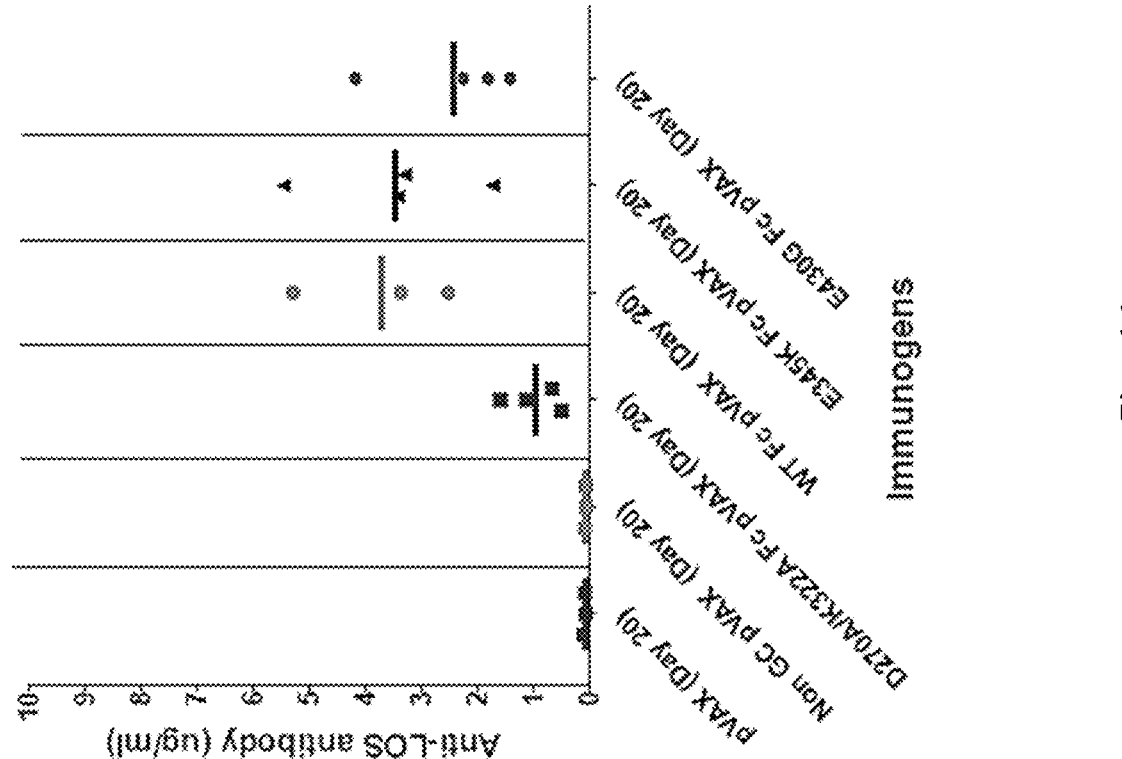
FIG. 11 depicts experimental results demonstrating the expression of anti-LOS antibody in lavage on day 20.

Example 1: Prophylactic Administration of DNA-Encoded Monoclonal Antibody 2C7 Facilitates Rapid Clearance of *N. Gonorrhoeae* Infection Passive administration of recombinant monoclonal antibody (mAb) 2C7, which recognizes a highly conserved epitope within the surface-exposed lipooligosaccharide (LOS) antigen, was previously shown to reduce bacterial burden and accelerate clearance of infection via complement activation (Gulati et al, PLoS Pathogens, 2013). The bactericidal activity was significantly enhanced through incorporation of specific residue modifications (E430G) within the Fc portion of 2C7 that enhances Fc hexamerization (Genmab's HexaBody® technology) and increased Clq engagement, resulting in clearance of colonization with a single intravenous dose as low as 1 µg (Gulati et al, PLoS Biology, 2019). The in vivo delivery of synthetic DNA plasmids encoding monoclonal antibody sequences (dMAbs) is a safe and cost-effective alternative to traditional mAb therapy. This strategy was applied to 2C7 using a dual-plasmid DNA system. To this end, optimized DNA constructs were generated encoding four versions of 2C7 that were previously shown to differentially affect complement activation in vivo: 1) wild type 2C7 (complement-activating); 2) 2C7-E430G (complement-enhancing variant); 3) 2C7-E345K (complement-enhancing variant) and 4) 2C7-D270A/K322A (NOCOMP, or complement-abrogating variant) (FIG. 1). All plasmids were successfully expressed in vitro and in vivo (FIG. 2 through FIG. 4), resulting in serum 2C7 IgG levels that far exceeded the previously determined mAb 2C7 therapeutic dose for at least 3 months post-immunization (Nude and JhD mice) (FIG. 5). Sera harvested from all 2C7 dMAb-injected mice were able to bind the LOS antigen and demonstrated potent in vitro bactericidal activity that correlated with serum 2C7 IgG levels (FIG. 6 and FIG. 7). The in vivo efficacies of these 2C7 dMAbs were subsequently evaluated using an established prophylactic model of *N. gonorrhoeae* infection. Following 2C7 dMAb administration, all groups of JhD mice generated high 2C7 IgG serum levels prior to intravaginal challenge with *N. gonorrhoeae* (strain FA1090) (FIG. 8). As expected, groups that received complement-activating 2C7 dMAb variants (wild type 2C7, 2C7-E430G and 2C7-E345K) demonstrated rapid control of infection relative to groups that received the complement-abrogating variant (2C7-D270A/K322A) or control plasmids (FIG. 9 through FIG. 11). These data verify the previously established complement-dependent protective capacity of mAb 2C7 and support further development of mAb 2C7-based immunotherapies using the versatile synthetic DNA platform.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

What is claimed is:

1. A nucleic acid molecule encoding one or more synthetic antibodies, wherein the nucleic acid molecule comprises at least one selected from the group consisting of
a) a nucleotide sequence encoding a synthetic antibody; and
b) a nucleotide sequence encoding a fragment of a synthetic antibody,
wherein the nucleotide sequence encodes an amino acid sequence having at least 97% identity over an entire length of the amino acid sequence selected from the group consisting of SEQ ID NO:2, SEQ ID NO: 4, SEQ ID NO: 6, SEQ ID NO:8, SEQ ID NO: 10, and SEQ ID NO: 12.

2. The nucleic acid molecule of claim 1, wherein the one or more synthetic antibodies is selected from the group consisting of: a monoclonal antibody, monofunctional antibody, bifunctional antibody, bispecific antibody, multivalent antibody, defucosylated antibody, non-fucosylated antibody, an immunoglobulin, and any combination thereof.

3. The nucleic acid molecule of claim 2, wherein the nucleic acid molecule encodes a fragment of a multivalent antibody, and further wherein the multivalent antibody is a hexameric antibody that forms in vivo.

4. The nucleic acid molecule of claim 3, wherein the nucleic acid molecule encodes a heavy chain of a multivalent antibody comprising a variation of at least one Fc residue selected from the group consisting of Q311, A339, E430, E345, D356, I253, S254,Y436, Q386, E382, and S440.

5. The nucleic acid molecule of claim 2, wherein the nucleic acid molecule encodes a heavy chain of a multivalent antibody comprising a variation of at least one Fc residue selected from the group consisting of E345R, E345K, E430G, and S440Y.

6. The nucleic acid molecule of claim 1, encoding one or more synthetic antibodies, or fragments thereof, wherein the nucleic acid molecule comprises at least one selected from the group consisting of
a) a nucleotide sequence encoding an anti-Neisseria gonorrhoeae synthetic antibody;
b) a nucleotide sequence encoding a fragment of an anti-Neisseria gonorrhoeae synthetic antibody;
c) a variant of a nucleotide sequence encoding an anti-Neisseria gonorrhoeae synthetic antibody; and
d) a variant of a nucleotide sequence encoding a fragment of an anti-Neisseria gonorrhoeae synthetic antibody.

7. The nucleic acid molecule of claim 6, comprising
a) a nucleotide sequence encoding a light chain of an anti-Neisseria gonorrhoeae antibody; and
b) a nucleotide sequence encoding a heavy chain of an anti-Neisseria gonorrhoeae antibody.

8. The nucleic acid molecule of claim 1, wherein the nucleic acid molecule comprises a nucleotide sequence having at least 97% identity over an entire length of the nucleic acid sequence consisting of SEQ ID NO:1.

9. The nucleic acid molecule of claim 1, wherein the nucleic acid molecule comprises a nucleotide sequence having at least 97% identity over an entire length of the nucleic acid sequence selected from the group consisting of SEQ ID NO:3, SEQ ID NO:5, SEQ ID NO:7, SEQ ID NO:9, and SEQ ID NO:11.

10. The nucleic acid molecule of claim 6, wherein the nucleotide sequence encodes a leader sequence.

11. The nucleic acid molecule of claim 1, wherein the nucleic acid molecule comprises an expression vector.

12. A composition comprising the nucleic acid molecule of claim 1.

13. The composition of claim 12 comprising at least one nucleic acid molecule comprising a nucleotide sequence encoding a light chain of an anti-Neisseria gonorrhoeae antibody and at least one nucleic acid molecule comprising a nucleotide sequence encoding a heavy chain of an anti-Neisseria gonorrhoeae antibody.

14. The composition of claim 12 comprising at least one nucleic acid molecule comprising a nucleotide sequence encoding an amino acid sequence having at least 97% identity over an entire length of the amino acid sequence SEQ ID NO: 2 and at least one nucleic acid molecule comprising a nucleotide sequence encoding an amino acid sequence having at least 97% identity over an entire length of the amino acid sequence selected from the group consisting of SEQ ID NO:4, SEQ ID NO:6, SEQ ID NO:8, SEQ ID NO:10, and SEQ ID NO:12.

15. The composition of claim 12, further comprising a pharmaceutically acceptable excipient.

16. A method of controlling Neisseria gonorrhoeae infection in a subject, the method comprising administering to the subject at least one expression vector wherein the at least one expression vector comprises nucleotide sequences encoding an antibody selected from the group consisting of:
a) an antibody comprising a heavy chain comprising the amino acid sequence as set forth in SEQ ID NO:4 and a light chain as set forth in SEQ ID NO:2;

b) an antibody comprising a heavy chain comprising the amino acid sequence as set forth in SEQ ID NO:6 and a light chain as set forth in SEQ ID NO:2; and c) an antibody comprising a heavy chain comprising the amino acid sequence as set forth in SEQ ID NO:8 and a light chain as set forth in SEQ ID NO:2.

17. A method of inducing an immune response against Neisseria gonorrhoeae in a subject, the method comprising administering to the subject at least one expression vector wherein the at least one expression vector comprises nucleotide sequences encoding an antibody selected from the group consisting of:

a) an antibody comprising a heavy chain comprising the amino acid sequence as set forth in SEQ ID NO:4 and a light chain as set forth in SEQ ID NO:2;

b) an antibody comprising a heavy chain comprising the amino acid sequence as set forth in SEQ ID NO:6 and a light chain as set forth in SEQ ID NO:2; and c) an antibody comprising a heavy chain comprising the amino acid sequence as set forth in SEQ ID NO:8 and a light chain as set forth in SEQ ID NO:2.

18. The method of claim 16, wherein the at least one expression vector comprises nucleotide sequences selected from the group consisting of:

a) a nucleotide sequence as set forth in SEQ ID NO:3 and a nucleotide sequence as set forth in SEQ ID NO:1;

b) a nucleotide sequence as set forth in SEQ ID NO:5 and a nucleotide sequence as set forth in SEQ ID NO:1; and c) a nucleotide sequence as set forth in SEQ ID NO:7 and a nucleotide sequence as set forth in SEQ ID NO:1.

19. The method of claim 17, wherein the at least one expression vector comprises nucleotide sequences selected from the group consisting of:

a) a nucleotide sequence as set forth in SEQ ID NO:3 and a nucleotide sequence as set forth in SEQ ID NO:1;

b) a nucleotide sequence as set forth in SEQ ID NO:5 and a nucleotide sequence as set forth in SEQ ID NO:1; and c) a nucleotide sequence as set forth in SEQ ID NO:7 and a nucleotide sequence as set forth in SEQ ID NO:1.

\* \* \* \* \*

SEQUENCE LISTING

<160> NUMBER OF SEQ ID NOS: 12

<210> SEQ ID NO 1
<211> LENGTH: 705
<212> TYPE: DNA
<213> ORGANISM: Artificial Sequence
<220> FEATURE:
<223> OTHER INFORMATION: Chemically synthesized, anti-2C7 light chain

<400> SEQUENCE: 1

```
atggtgctgc agactcaggt gtttatttca ctgctgctgt ggatttcagg ggcttacggc      60
caggtcgtgg tcactcagga gagcgcactg accacatccc caggcgagac agtgacactg     120
acctgccgga gctccacagg agcagtgacc acatctaact acgccaattg ggtgcaggag     180
aagcccgacc acctgttcac cggcctgatc ggcggcatca acaataggg gccaggagtg     240 ccagcaaggt tcagcggctc cctgatcggc gacaaggccg ccctgacaat caccggagca     300
cagacagagg atgaggccat ctacttctgc gccctgtggt atagcaacca ctgggtgttt     360
ggcggcggaa caaagctgac cgtgctgggc cagcctaagg ccaacccaac agtgaccctg     420
ttccctccca gcagcgagga gctgcaggcc aataaggcca ccctggtgtg cctgatctct     480 gactttacc ctggagcagt gaccgtggca tggaaggcag atggcagccc cgtgaaggca     540
ggagtggaga acaacaaagcc ttccaagcag tctaacaata gtacgccgc ctcctcttat     600 ctgagcctga cccccgagca gtggaagtcc caccgctctt atagctgcca ggtcacccat     660
gaaggaagca ccgtggagaa gactgtcgcc ccaaccgaat gtagc                     705
```

<210> SEQ ID NO 2
<211> LENGTH: 235
<212> TYPE: PRT
<213> ORGANISM: Artificial Sequence
<220> FEATURE:
<223> OTHER INFORMATION: Chemically synthesized, anti-2C7 light chain

<400> SEQUENCE: 2

```
Met Val Leu Gln Thr Gln Val Phe Ile Ser Leu Leu Leu Trp Ile Ser
1               5                   10                  15

Gly Ala Tyr Gly Gln Val Val Val Thr Gln Glu Ser Ala Leu Thr Thr
            20                  25                  30

Ser Pro Gly Glu Thr Val Thr Leu Thr Cys Arg Ser Ser Thr Gly Ala
        35                  40                  45

Val Thr Thr Ser Asn Tyr Ala Asn Trp Val Gln Glu Lys Pro Asp His
    50                  55                  60

Leu Phe Thr Gly Leu Ile Gly Gly Ile Asn Asn Arg Ala Pro Gly Val
65                  70                  75                  80

Pro Ala Arg Phe Ser Gly Ser Leu Ile Gly Asp Lys Ala Ala Leu Thr
                85                  90                  95

Ile Thr Gly Ala Gln Thr Glu Asp Glu Ala Ile Tyr Phe Cys Ala Leu
            100                 105                 110

Trp Tyr Ser Asn His Trp Val Phe Gly Gly Gly Thr Lys Leu Thr Val
        115                 120                 125

Leu Gly Gln Pro Lys Ala Asn Pro Thr Val Thr Leu Phe Pro Pro Ser
    130                 135                 140

Ser Glu Glu Leu Gln Ala Asn Lys Ala Thr Leu Val Cys Leu Ile Ser
145                 150                 155                 160

Asp Phe Tyr Pro Gly Ala Val Thr Val Ala Trp Lys Ala Asp Gly Ser
                165                 170                 175
```

-continued

```
Pro Val Lys Ala Gly Val Glu Thr Thr Lys Pro Ser Lys Gln Ser Asn
        180                 185                 190

Asn Lys Tyr Ala Ala Ser Ser Tyr Leu Ser Leu Thr Pro Glu Gln Trp
        195                 200                 205

Lys Ser His Arg Ser Tyr Ser Cys Gln Val Thr His Glu Gly Ser Thr
    210                 215                 220

Val Glu Lys Thr Val Ala Pro Thr Glu Cys Ser
225                 230                 235
```

```
<210> SEQ ID NO 3
<211> LENGTH: 1398
<212> TYPE: DNA
<213> ORGANISM: Artificial Sequence
<220> FEATURE:
<223> OTHER INFORMATION: Chemically synthesized, anti-2C7 heavy chain

<400> SEQUENCE: 3
atggattgga catggaggat tctgtttctg gtcgccgccg ctacaggaac ccacgccgaa      60
gtgcagctgc agcagtcagg ccccgaactg gtgaagcctg gcagctccgt gaagatcagc     120
tgcaagggct ccggctatac cttcacagac tacaacatgg agtgggtgaa gcagtctcac     180
ggcaagagcc tggagtggat cggcgtgatc aatccaaaca ataggttcac ctcctataac     240
cagaacttca ggggcaaggc caccctgaca gtggacaagt ctagctccac cgcctatatg     300
gacctgagga gcctgaccag cgaggattcc gccgtgtact tctgcgcagg cagccgctgg     360
taccagtatg attactgggg ccagggcacc acactgaccg tgtctagcgc ctccacaaag     420
ggaccaagcg tgttcccact ggcaccctcc tctaagtcca cctctggcgg cacagccgcc     480
ctgggctgtc tggtgaagga ttacttccca gagcccgtga ccgtgtcttg aacagcggc     540 gccctgacct ctggagtgca cacatttcca gccgtgctgc agagctccgg cctgtatagc     600
ctgtctagcg tggtgaccgt gccctcctct agcctgggca cccagacata catctgcaac     660
gtgaatcaca agccatctaa tacaaaggtg gacaagaagg tggagcccaa gagctgtgat     720
aagacccaca catgccctcc ctgtcctgca ccagagctgc tgggcggccc atccgtgttc     780
ctgtttccac ccaagcctaa ggacaccctg atgatctcca ggacccccga ggtgacatgc     840
gtggtggtgg acgtgtctca cgaggacccc gaggtgaagt ttaactggta cgtggatggc     900
gtggaggtgc acaatgccaa gacaaagcct cgggaggagc agtataacag cacctaccgc     960
gtggtgtccg tgctgacagt gctgcaccag gactggctga cggcaagga gtacaagtgc    1020 aaggtgagca ataaggccct gcccgcccct atcgagaaga ccatctccaa ggccaagggc    1080
cagcctaggg agccacaggt gtatacactg cctccaagca gagacgagct gaccaagaac    1140
caggtgtccc tgacatgtct ggtgaagggc ttctaccctt ccgatatcgc cgtggagtgg    1200
gagtctaatg ccagccaga aacaattat aagaccacac ccctgtgct ggactccgat    1260 ggctctttct ttctgtactc taagctgacc gtggataaga gcaggtggca gcaggcaac    1320 gtgtttagct gttccgtgat gcacgaagcc ctgcacaacc attacaccca gaagtcactg    1380
tccctgagcc ccggaaag                                                 1398
```

```
<210> SEQ ID NO 4
<211> LENGTH: 466
<212> TYPE: PRT
<213> ORGANISM: Artificial Sequence
<220> FEATURE:
<223> OTHER INFORMATION: Chemically synthesized, anti-2C7 heavy chain

<400> SEQUENCE: 4
```

-continued

```
Met Asp Trp Thr Trp Arg Ile Leu Phe Leu Val Ala Ala Ala Thr Gly
1               5                   10                  15

Thr His Ala Glu Val Gln Leu Gln Gln Ser Gly Pro Glu Leu Val Lys
            20                  25                  30

Pro Gly Ser Ser Val Lys Ile Ser Cys Lys Gly Ser Gly Tyr Thr Phe
        35                  40                  45

Thr Asp Tyr Asn Met Glu Trp Val Lys Gln Ser His Gly Lys Ser Leu
    50                  55                  60

Glu Trp Ile Gly Val Ile Asn Pro Asn Asn Arg Phe Thr Ser Tyr Asn
65                  70                  75                  80

Gln Asn Phe Arg Gly Lys Ala Thr Leu Thr Val Asp Lys Ser Ser Ser
            85                  90                  95

Thr Ala Tyr Met Asp Leu Arg Ser Leu Thr Ser Glu Asp Ser Ala Val
            100                 105                 110

Tyr Phe Cys Ala Gly Ser Arg Trp Tyr Gln Tyr Asp Tyr Trp Gly Gln
        115                 120                 125

Gly Thr Thr Leu Thr Val Ser Ser Ala Ser Thr Lys Gly Pro Ser Val
    130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
            165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
            195                 200                 205

Ser Ser Ser Leu Gly Thr Gln Thr Tyr Ile Cys Asn Val Asn His Lys
    210                 215                 220

Pro Ser Asn Thr Lys Val Asp Lys Lys Val Glu Pro Lys Ser Cys Asp
225                 230                 235                 240

Lys Thr His Thr Cys Pro Pro Cys Pro Ala Pro Glu Leu Leu Gly Gly
            245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
    275                 280                 285

Asp Pro Glu Val Lys Phe Asn Trp Tyr Val Asp Gly Val Glu Val His
    290                 295                 300

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
            325                 330                 335

Glu Tyr Lys Cys Lys Val Ser Asn Lys Ala Leu Pro Ala Pro Ile Glu
            340                 345                 350

Lys Thr Ile Ser Lys Ala Lys Gly Gln Pro Arg Glu Pro Gln Val Tyr
            355                 360                 365

Thr Leu Pro Pro Ser Arg Asp Glu Leu Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
            405                 410                 415
```

```
Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
    450                 455                 460

Gly Lys
465
```

```
<210> SEQ ID NO 5
<211> LENGTH: 1398
<212> TYPE: DNA
<213> ORGANISM: Artificial Sequence
<220> FEATURE:
<223> OTHER INFORMATION: Chemically synthesized, anti-2C7 E430G heavy
      chain

<400> SEQUENCE: 5
atggattgga catggaggat tctgtttctg gtcgccgccg ctacaggaac ccacgccgaa      60
gtgcagctgc agcagtcagg ccccgaactg gtgaagcctg gcagctccgt gaagatcagc     120
tgcaagggct ccggctatac cttcacagac tacaacatgg agtgggtgaa gcagtctcac     180
ggcaagagcc tggagtggat cggcgtgatc aatccaaaca ataggttcac ctcctataac     240
cagaacttca ggggcaaggc caccctgaca gtggacaagt ctagtccac cgcctatatg      300 gacctgagga gcctgaccag cgaggattcc gccgtgtact tctgcgcagg cagccgctgg     360
taccagtatg attactgggg ccagggcacc acactgaccg tgtctagcgc ctccacaaag     420
ggaccaagcg tgttcccact ggcaccctcc tctaagtcca cctctggcgg cacagccgcc     480
ctgggctgtc tggtgaagga ttacttccca gagcccgtga ccgtgtcttg gaacagcggc     540
gccctgacct ctggagtgca cacatttcca gccgtgctgc agagctccgg cctgtatagc     600
ctgtctagcg tggtgaccgt gccctcctct agcctgggca cccagacata catctgcaac     660
gtgaatcaca agccatctaa tacaaaggtg gacaagaagg tggagcccaa gagctgtgat     720
aagacccaca catgccctcc ctgtcctgca ccagagctgc tgggcggccc atccgtgttc     780
ctgtttccac ccaagcctaa ggacaccctg atgatctcca ggacccccga ggtgacatgc     840
gtggtggtgg acgtgtctca cgaggacccc gaggtgaagt ttaactggta cgtggatggc     900
gtggaggtgc acaatgccaa gacaaagcct cgggaggagc agtataacag cacctaccgc     960
gtggtgtccg tgctgacagt gctgcaccag gactggctga acggcaagga gtacaagtgc    1020
aaggtgagca ataaggccct gcccgcccct atcgagaaga ccatctccaa ggccaagggc    1080
cagcctaggg agccacaggt gtatacactg cctccaagca gagacgagct gaccaagaac    1140
caggtgtccc tgacatgtct ggtgaagggc ttctaccctt ccgatatcgc cgtggagtgg    1200
gagtctaatg ccagccaga gaacaattat aagaccacac ccctgtgct ggactccgat      1260 ggctctttct ttctgtactc taagctgacc gtggataaga gcaggtggca gcagggcaac    1320
gtgtttagct gttccgtgat gcacggcgcc ctgcacaacc attacaccca gaagtcactg    1380
tccctgagcc ccggaaag                                                  1398
```

```
<210> SEQ ID NO 6
<211> LENGTH: 466
<212> TYPE: PRT
<213> ORGANISM: Artificial Sequence
<220> FEATURE:
<223> OTHER INFORMATION: Chemically synthesized, anti-2C7 E430G heavy
      chain
```

-continued

<400> SEQUENCE: 6

Met Asp Trp Thr Trp Arg Ile Leu Phe Leu Val Ala Ala Ala Thr Gly
1               5                   10                  15

Thr His Ala Glu Val Gln Leu Gln Gln Ser Gly Pro Glu Leu Val Lys
                20                  25                  30

Pro Gly Ser Ser Val Lys Ile Ser Cys Lys Gly Ser Gly Tyr Thr Phe
            35                  40                  45

Thr Asp Tyr Asn Met Glu Trp Val Lys Gln Ser His Gly Lys Ser Leu
        50                  55                  60

Glu Trp Ile Gly Val Ile Asn Pro Asn Asn Arg Phe Thr Ser Tyr Asn
65                  70                  75                  80

Gln Asn Phe Arg Gly Lys Ala Thr Leu Thr Val Asp Lys Ser Ser Ser
                85                  90                  95

Thr Ala Tyr Met Asp Leu Arg Ser Leu Thr Ser Glu Asp Ser Ala Val
            100                 105                 110

Tyr Phe Cys Ala Gly Ser Arg Trp Tyr Gln Tyr Asp Tyr Trp Gly Gln
        115                 120                 125

Gly Thr Thr Leu Thr Val Ser Ser Ala Ser Thr Lys Gly Pro Ser Val
    130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Ser Leu Gly Thr Gln Thr Tyr Ile Cys Asn Val Asn His Lys
    210                 215                 220

Pro Ser Asn Thr Lys Val Asp Lys Lys Val Glu Pro Lys Ser Cys Asp
225                 230                 235                 240

Lys Thr His Thr Cys Pro Pro Cys Pro Ala Pro Glu Leu Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Lys Phe Asn Trp Tyr Val Asp Gly Val Glu Val His
    290                 295                 300

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Ala Leu Pro Ala Pro Ile Glu
            340                 345                 350

Lys Thr Ile Ser Lys Ala Lys Gly Gln Pro Arg Glu Pro Gln Val Tyr
        355                 360                 365

Thr Leu Pro Pro Ser Arg Asp Glu Leu Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val

-continued

```
                     405                410                415
```

Leu Asp Ser Asp Gly Ser Phe Phe Leu Tyr Ser Lys Leu Thr Val Asp
            420                425                430

Lys Ser Arg Trp Gln Gln Gly Asn Val Phe Ser Cys Ser Val Met His
        435                440                445

Gly Ala Leu His Asn His Tyr Thr Gln Lys Ser Leu Ser Leu Ser Pro
    450                455                460

Gly Lys
465

<210> SEQ ID NO 7
<211> LENGTH: 1398
<212> TYPE: DNA
<213> ORGANISM: Artificial Sequence
<220> FEATURE:
<223> OTHER INFORMATION: Chemically synthesized, anti-2C7 E345K heavy
      chain

<400> SEQUENCE: 7
atggattgga catggaggat tctgtttctg gtcgccgccg ctacaggaac ccacgccgaa      60
gtgcagctgc agcagtcagg ccccgaactg gtgaagcctg gcagctccgt gaagatcagc     120
tgcaagggct ccggctatac cttcacagac tacaacatgg agtgggtgaa gcagtctcac     180
ggcaagagcc tggagtggat cggcgtgatc aatccaaaca ataggttcac ctcctataac     240
cagaacttca ggggcaaggc caccctgaca gtggacaagt ctagctccac cgcctatatg     300
gacctgagga gcctgaccag cgaggattcc gccgtgtact ctgcgcagg cagccgctgg      360 taccagtatg attactgggg ccagggcacc acactgaccg tgtctagcgc ctccacaaag     420
ggaccaagcg tgttcccact ggcaccctcc tctaagtcca cctctggcgg cacagccgcc     480
ctgggctgtc tggtgaagga ttacttccca gagcccgtga ccgtgtcttg aacagcggc      540 gccctgacct ctggagtgca cacatttcca gccgtgctgc agagctccgg cctgtatagc     600
ctgtctagcg tggtgaccgt gccctcctct agcctgggca cccagacata catctgcaac     660
gtgaatcaca agccatctaa tacaaaggtg gacaagaagg tggagcccaa gagctgtgat     720
aagacccaca catgccctcc ctgtcctgca ccagagctgc tgggcggccc atccgtgttc     780
ctgtttccac ccaagcctaa ggacaccctg atgatctcca ggacccccga ggtgacatgc     840
gtggtggtgg acgtgtctca cgaggacccc gaggtgaagt ttaactggta cgtggatggc     900
gtggaggtgc acaatgccaa gacaaagcct cgggaggagc agtataacag cacctaccgc     960
gtggtgtccg tgctgacagt gctgcaccag gactggctga cggcaagga gtacaagtgc     1020 aaggtgagca taaggccct gcccgcccct atcgagaaga ccatctccaa ggccaagggc     1080
cagcctagga agccacaggt gtatacactg cctccaagca gagacgagct gaccaagaac     1140
caggtgtccc tgacatgtct ggtgaagggc ttctacccct ccgatatcgc cgtggagtgg     1200
gagtctaatg ccagccaga gaacaattat aagaccacac ccctgtgct ggactccgat      1260 ggctctttct ttctgtactc taagctgacc gtggataaga gcaggtggca gcagggcaac     1320
gtgtttagct gttccgtgat gcacgaagcc ctgcacaacc attacccca gaagtcactg      1380 tccctgagcc ccggaaag                                                  1398

<210> SEQ ID NO 8
<211> LENGTH: 466
<212> TYPE: PRT
<213> ORGANISM: Artificial Sequence
<220> FEATURE:
```

<223> OTHER INFORMATION: Chemically synthesized, anti-2C7 E345K heavy
      chain

<400> SEQUENCE: 8

```
Met Asp Trp Thr Trp Arg Ile Leu Phe Leu Val Ala Ala Ala Thr Gly
1               5                   10                  15

Thr His Ala Glu Val Gln Leu Gln Gln Ser Gly Pro Glu Leu Val Lys
            20                  25                  30

Pro Gly Ser Ser Val Lys Ile Ser Cys Lys Gly Ser Gly Tyr Thr Phe
        35                  40                  45

Thr Asp Tyr Asn Met Glu Trp Val Lys Gln Ser His Gly Lys Ser Leu
    50                  55                  60

Glu Trp Ile Gly Val Ile Asn Pro Asn Asn Arg Phe Thr Ser Tyr Asn
65                  70                  75                  80

Gln Asn Phe Arg Gly Lys Ala Thr Leu Thr Val Asp Lys Ser Ser Ser
                85                  90                  95

Thr Ala Tyr Met Asp Leu Arg Ser Leu Thr Ser Glu Asp Ser Ala Val
            100                 105                 110

Tyr Phe Cys Ala Gly Ser Arg Trp Tyr Gln Tyr Asp Tyr Trp Gly Gln
        115                 120                 125

Gly Thr Thr Leu Thr Val Ser Ser Ala Ser Thr Lys Gly Pro Ser Val
    130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
            165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
            195                 200                 205

Ser Ser Ser Leu Gly Thr Gln Thr Tyr Ile Cys Asn Val Asn His Lys
    210                 215                 220

Pro Ser Asn Thr Lys Val Asp Lys Lys Val Glu Pro Lys Ser Cys Asp
225                 230                 235                 240

Lys Thr His Thr Cys Pro Pro Cys Pro Ala Pro Glu Leu Leu Gly Gly
            245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
    275                 280                 285

Asp Pro Glu Val Lys Phe Asn Trp Tyr Val Asp Gly Val Glu Val His
    290                 295                 300

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
            325                 330                 335

Glu Tyr Lys Cys Lys Val Ser Asn Lys Ala Leu Pro Ala Pro Ile Glu
            340                 345                 350

Lys Thr Ile Ser Lys Ala Lys Gly Gln Pro Arg Lys Pro Gln Val Tyr
            355                 360                 365

Thr Leu Pro Pro Ser Arg Asp Glu Leu Thr Lys Asn Gln Val Ser Leu
    370                 375                 380

Thr Cys Leu Val Lys Gly Phe Tyr Pro Ser Asp Ile Ala Val Glu Trp
385                 390                 395                 400
```

```
Glu Ser Asn Gly Gln Pro Glu Asn Asn Tyr Lys Thr Thr Pro Pro Val
            405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
    450                 455                 460

Gly Lys
465
```

<210> SEQ ID NO 9
<211> LENGTH: 1398
<212> TYPE: DNA
<213> ORGANISM: Artificial Sequence
<220> FEATURE:
<223> OTHER INFORMATION: Chemically synthesized, anti-2C7 RGY heavy
      chain

<400> SEQUENCE: 9

```
atggattgga catggaggat tctgtttctg gtcgccgccg ctacaggaac ccacgccgaa      60
gtgcagctgc agcagtcagg ccccgaactg gtgaagcctg gcagctccgt gaagatcagc     120
tgcaagggct ccggctatac cttcacagac tacaacatgg agtgggtgaa gcagtctcac     180
ggcaagagcc tggagtggat cggcgtgatc aatccaaaca taggttcac tcctataac      240 cagaacttca ggggcaaggc caccctgaca gtggacaagt ctagctccac cgcctatatg     300
gacctgagga gcctgaccag cgaggattcc gccgtgtact tctgcgcagg cagccgctgg     360
taccagtatg attactgggg ccagggcacc acactgaccg tgtctagcgc ctccacaaag     420
ggaccaagcg tgttcccact ggcaccctcc tctaagtcca cctctggcgg cacagccgcc     480
ctgggctgtc tggtgaagga ttacttccca gagcccgtga ccgtgtcttg aacagcggc      540 gccctgacct ctggagtgca cacatttcca gccgtgctgc agagctccgg cctgtatagc     600
ctgtctagcg tggtgaccgt gccctcctct agcctgggca cccagacata catctgcaac     660
gtgaatcaca agccatctaa tacaaaggtg gacaagaagg tggagcccaa gagctgtgat     720
aagacccaca catgccctcc ctgtcctgca ccagagctgc tgggcggccc atccgtgttc     780
ctgtttccac ccaagcctaa ggacaccctg atgatctcca ggacccccga ggtgacatgc     840
gtggtggtgg acgtgtctca cgaggacccc gaggtgaagt ttaactggta cgtggatggc     900
gtggaggtgc acaatgccaa gacaaagcct cgggaggagc agtataacag cacctaccgc     960
gtggtgtccg tgctgacagt gctgcaccag gactggctga acggcaagga gtacaagtgc    1020
aaggtgagca taaggcccct gcccgcccct atcgagaaga ccatctccaa ggccaagggc    1080
cagcctagga ggccacaggt gtatacactg cctccaagca gagacgagct gaccaagaac    1140
caggtgtccc tgacatgtct ggtgaagggc ttctacccct tccgatatcg cgtggagtgg    1200
gagtctaatg ccagccaga aacaattat aagaccacac ccctgtgct ggactccgat      1260 ggctctttct ttctgtactc taagctgacc gtggataaga gcaggtggca gcagggcaac    1320
gtgtttagct gttccgtgat gcacggcgcc ctgcacaacc attacacca gaagtacctg     1380 tccctgagcc ccggaaag                                                   1398
```

<210> SEQ ID NO 10
<211> LENGTH: 466
<212> TYPE: PRT

```
<213> ORGANISM: Artificial Sequence
<220> FEATURE:
<223> OTHER INFORMATION: Chemically synthesized, anti-2C7 RGY heavy
      chain

<400> SEQUENCE: 10

Met Asp Trp Thr Trp Arg Ile Leu Phe Leu Val Ala Ala Ala Thr Gly
1               5                   10                  15

Thr His Ala Glu Val Gln Leu Gln Gln Ser Gly Pro Glu Leu Val Lys
            20                  25                  30

Pro Gly Ser Ser Val Lys Ile Ser Cys Lys Gly Ser Gly Tyr Thr Phe
            35                  40                  45

Thr Asp Tyr Asn Met Glu Trp Val Lys Gln Ser His Gly Lys Ser Leu
        50                  55                  60

Glu Trp Ile Gly Val Ile Asn Pro Asn Asn Arg Phe Thr Ser Tyr Asn
65                  70                  75                  80

Gln Asn Phe Arg Gly Lys Ala Thr Leu Thr Val Asp Lys Ser Ser Ser
                85                  90                  95

Thr Ala Tyr Met Asp Leu Arg Ser Leu Thr Ser Glu Asp Ser Ala Val
            100                 105                 110

Tyr Phe Cys Ala Gly Ser Arg Trp Tyr Gln Tyr Asp Tyr Trp Gly Gln
            115                 120                 125

Gly Thr Thr Leu Thr Val Ser Ser Ala Ser Thr Lys Gly Pro Ser Val
        130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
            165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
            195                 200                 205

Ser Ser Ser Leu Gly Thr Gln Thr Tyr Ile Cys Asn Val Asn His Lys
        210                 215                 220

Pro Ser Asn Thr Lys Val Asp Lys Lys Val Glu Pro Lys Ser Cys Asp
225                 230                 235                 240

Lys Thr His Thr Cys Pro Pro Cys Pro Ala Pro Glu Leu Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Lys Phe Asn Trp Tyr Val Asp Gly Val Glu Val His
        290                 295                 300

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
            325                 330                 335

Glu Tyr Lys Cys Lys Val Ser Asn Lys Ala Leu Pro Ala Pro Ile Glu
            340                 345                 350

Lys Thr Ile Ser Lys Ala Lys Gly Gln Pro Arg Arg Pro Gln Val Tyr
            355                 360                 365

Thr Leu Pro Pro Ser Arg Asp Glu Leu Thr Lys Asn Gln Val Ser Leu
        370                 375                 380
```

-continued

```
Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Lys Leu Thr Val Asp
                420                 425                 430

Lys Ser Arg Trp Gln Gln Gly Asn Val Phe Ser Cys Ser Val Met His
        435                 440                 445

Gly Ala Leu His Asn His Tyr Thr Gln Lys Tyr Leu Ser Leu Ser Pro
    450                 455                 460

Gly Lys
465
```

```
<210> SEQ ID NO 11
<211> LENGTH: 1398
<212> TYPE: DNA
<213> ORGANISM: Artificial Sequence
<220> FEATURE:
<223> OTHER INFORMATION: Chemically synthesized, anti-2C7 D270A/K322A
      heavy chain

<400> SEQUENCE: 11
atggattgga catggaggat tctgtttctg gtcgccgccg ctacaggaac ccacgccgaa       60
gtgcagctgc agcagtcagg ccccgaactg gtgaagcctg gcagctccgt gaagatcagc      120
tgcaagggct ccggctatac cttcacagac tacaacatgg agtgggtgaa gcagtctcac      180
ggcaagagcc tggagtggat cggcgtgatc aatccaaaca ataggttcac ctcctataac      240
cagaacttca ggggcaaggc caccctgaca gtggacaagt ctagctccac cgcctatatg      300
gacctgagga gcctgaccag cgaggattcc gccgtgtact ctgcgcagg cagccgctgg      360 taccagtatg attactgggg ccagggcacc acactgaccg tgtctagcgc ctccacaaag      420
ggaccaagcg tgttcccact ggcaccctcc tctaagtcca cctctggcgg cacagccgcc      480
ctgggctgtc tggtgaagga ttacttccca gagcccgtga ccgtgtcttg aacagcggc      540 gccctgacct ctggagtgca cacatttcca gccgtgctgc agagctccgg cctgtatagc      600
ctgtctagcg tggtgaccgt gccctcctct agcctgggca cccagacata catctgcaac      660
gtgaatcaca gccatctaa tacaaaggtg gacaagaagg tggagcccaa gagctgtgat      720
aagacccaca catgccctcc ctgtcctgca ccagagctgc tgggcggccc atccgtgttc      780
ctgtttccac ccaagcctaa ggacaccctg atgatctcca ggaccccga ggtgacatgc      840 gtggtggtgg acgtgtctca cgaggccccc gaggtgaagt ttaactggta cgtggatggc      900
gtggaggtgc acaatgccaa gacaaagcct cgggaggagc agtataacag cacctaccgc      960
gtggtgtccg tgctgacagt gctgcaccag gactggctga cggcaagga gtacaagtgc     1020 gccgtgagca ataaggccct gcccgcccct atcgagaaga ccatctccaa ggccaagggc     1080
cagcctaggg agccacaggt gtatacactg cctccaagca gagacgagct gaccaagaac     1140
caggtgtccc tgacatgtct ggtgaagggc ttctaccctt ccgatatcgc cgtggagtgg     1200
gagtctaatg ccagccaga gaacaattat aagaccacac ccctgtgct ggactccgat     1260 ggctctttct ttctgtactc taagctgacc gtggataaga gcaggtggca gcagggcaac     1320
gtgtttagct gttccgtgat gcacgaagcc ctgcacaacc attacaccca gaagtcactg     1380
tccctgagcc ccggaaag                                                   1398

<210> SEQ ID NO 12
```

<211> LENGTH: 466
<212> TYPE: PRT
<213> ORGANISM: Artificial Sequence
<220> FEATURE:
<223> OTHER INFORMATION: Chemically synthesized, anti-2C7 D270A/K322A
      heavy chain

<400> SEQUENCE: 12

Met Asp Trp Thr Trp Arg Ile Leu Phe Leu Val Ala Ala Ala Thr Gly
1               5                   10                  15

Thr His Ala Glu Val Gln Leu Gln Gln Ser Gly Pro Glu Leu Val Lys
            20                  25                  30

Pro Gly Ser Ser Val Lys Ile Ser Cys Lys Gly Ser Gly Tyr Thr Phe
        35                  40                  45

Thr Asp Tyr Asn Met Glu Trp Val Lys Gln Ser His Gly Lys Ser Leu
    50                  55                  60

Glu Trp Ile Gly Val Ile Asn Pro Asn Asn Arg Phe Thr Ser Tyr Asn
65                  70                  75                  80

Gln Asn Phe Arg Gly Lys Ala Thr Leu Thr Val Asp Lys Ser Ser Ser
                85                  90                  95

Thr Ala Tyr Met Asp Leu Arg Ser Leu Thr Ser Glu Asp Ser Ala Val
            100                 105                 110

Tyr Phe Cys Ala Gly Ser Arg Trp Tyr Gln Tyr Asp Tyr Trp Gly Gln
            115                 120                 125

Gly Thr Thr Leu Thr Val Ser Ser Ala Ser Thr Lys Gly Pro Ser Val
    130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
            195                 200                 205

Ser Ser Ser Leu Gly Thr Gln Thr Tyr Ile Cys Asn Val Asn His Lys
    210                 215                 220

Pro Ser Asn Thr Lys Val Asp Lys Lys Val Glu Pro Lys Ser Cys Asp
225                 230                 235                 240

Lys Thr His Thr Cys Pro Pro Cys Pro Ala Pro Glu Leu Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
            275                 280                 285

Ala Pro Glu Val Lys Phe Asn Trp Tyr Val Asp Gly Val Glu Val His
    290                 295                 300

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
            325                 330                 335

Glu Tyr Lys Cys Ala Val Ser Asn Lys Ala Leu Pro Ala Pro Ile Glu
            340                 345                 350

Lys Thr Ile Ser Lys Ala Lys Gly Gln Pro Arg Glu Pro Gln Val Tyr
            355                 360                 365

Thr Leu Pro Pro Ser Arg Asp Glu Leu Thr Lys Asn Gln Val Ser Leu

```
          370              375              380

Thr Cys Leu Val Lys Gly Phe Tyr Pro Ser Asp Ile Ala Val Glu Trp
385              390              395              400

Glu Ser Asn Gly Gln Pro Glu Asn Asn Tyr Lys Thr Thr Pro Pro Val
              405              410              415

Leu Asp Ser Asp Gly Ser Phe Phe Leu Tyr Ser Lys Leu Thr Val Asp
              420              425              430

Lys Ser Arg Trp Gln Gln Gly Asn Val Phe Ser Cys Ser Val Met His
          435              440              445

Glu Ala Leu His Asn His Tyr Thr Gln Lys Ser Leu Ser Leu Ser Pro
      450              455              460

Gly Lys
465
```